United States Patent
Dou et al.

(10) Patent No.: US 6,692,927 B2
(45) Date of Patent: Feb. 17, 2004

(54) BAX DEGRADATION INVOLVEMENT IN TUMOR SURVIVAL AND PROGRESSION

(75) Inventors: Ping Dou, Tampa, FL (US); Benyi Li, Tampa, FL (US)

(73) Assignee: University of South Florida, Tampa, FL (US)

(*) Notice: Subject to any disclaimer, the term of this patent is extended or adjusted under 35 U.S.C. 154(b) by 29 days.

(21) Appl. No.: 09/799,253

(22) Filed: Mar. 5, 2001

(65) Prior Publication Data

US 2002/0102621 A1 Aug. 1, 2002

Related U.S. Application Data

(60) Provisional application No. 60/186,895, filed on Mar. 3, 2000, and provisional application No. 60/217,264, filed on Jul. 11, 2000.

(51) Int. Cl.[7] ......................... C12Q 1/00; G01N 33/567; G01N 33/574; G01N 33/53; G01N 33/543
(52) U.S. Cl. ......................... 435/7.23; 435/4; 435/7.21; 435/7.92; 436/8; 436/63; 436/64; 436/86; 436/164; 436/174; 530/300; 530/350; 530/386; 530/387.1; 530/387.7
(58) Field of Search .................................. 530/300, 350, 530/386, 387.1, 387.7; 436/8, 63, 64, 86, 164, 174; 435/4, 7.21, 7.23, 7.92

(56) References Cited

U.S. PATENT DOCUMENTS 5,691,179 A * 11/1997 Korsmeyer

OTHER PUBLICATIONS

Li and Dou, Bax degradation by the ubiquitin/proteasome–dependent pathway: Involvement in tumor survival and progression. Proc. Natl. Acad. Sci. USA. 97(8):3850–3855, Apr. 11, 2000.*

An, B., and Dou, Q.P. "Cleavage of retinoblastoma protein during apoptosis: an interleukin 1 beta–converting enzyme–like protease as candidate", Cancer Res. (1996) vol. 56, No. 3, pp. 438–442.

An, B., et al., "Novel dipeptidyl proteasome inhibitors overcome Bcl–2 protective function and selectively accumulate the cyclin–dependent kinase inhibitor p27 and induce apoptosis in transformed, but not normal human fibroblasts", Cell Death Differ. (1998), vol. 12, pp. 1062–1075.

Antonsson, B., et al., "Inhibition of Bax channel–forming activity by Bcl–2", Science (1997), vol. 277, No. 5324, pp. 370–372.

Bargou, R.C., et al., Overexpression of the death–promoting gene bax–alpha which is downregulated in breast cancer restores sensitivity to different apoptotic stimuli and reduces tumor growth in SCID mice, J Clin Invest. (1996), vol. 97, No. 11, pp. 2651–2659.

Barrell, B.G., et al., "A Different Genetic Code in Human Mitochondria", Nature (1979), vol. 282, pp. 189–194.

Bedi, A., et al., "Inhibition of apoptosis by BCR–ABL in chronic myeloid leukemia", Blood (1994), vol. 83, No. 8, pp. 2038–2044.

Binder, C., et al., "Expression of Bax in relation to Bcl–2 and other predictive parameters in breast cancer", Ann Oncol. (1996), vol. 7, No. 2, pp. 129–133.

Blagosklonny, M.V., et al., "Proteasome–dependent regulation of p21WAF1/CIP1 expression", Biochem Biophys Res Commun. (1996), vol. 227, No. 2, p. 564–9.

Bossy–Wetzel, E., et al., "Mitochondrial cytochrome c release in apoptosis occurs upstream of DEVD–specific caspase activation and independently of mitochondrial transmembrane depolarization", EMBO J. (1998) vol. 17, No. 1, pp. 37–49.

Chang, Y.C., et al., "mdm2 and bax, downstream mediators of the p53 response, are degraded by the ubiquitin–proteasome pathway", Cell Growth Differ. (1998), vol. 9, No. 1, pp. 79–84.

Chau, V., et al., "A multiquitin chain is confined to specific lysine in a targeted short–lived protein", Science (1989), vol. 243, No. 4898, pp. 1576–1583.

Chen, G., et al., "Nix and Nip3 from a subfamily of pro–apoptotic mitochondrial proteins", J Biol Chem. (1999), vol. 274, No. 1, pp. 7–10.

Chen, G., et al., "The E1B 19K/Bcl–2–binding protein Nip3 is a dimeric mitochondrial protein that activates apoptosis", J Exp Med. (1997), vol. 186, No. 12, pp. 1975–1983.

Chen, K., et al., "Double Immunoenzyme staining method for analysis of tissue and blood lymphocyte subsets with monoclonal antibodies", Lab Invest. (1987), vol. 56, No. 1, pp. 114–119.

(List continued on next page.)

Primary Examiner—Alana M. Harris
(74) Attorney, Agent, or Firm—Saliwanchik, Lloyd & Saliwanchik

(57) ABSTRACT

According to the present invention, there is provided an assay for determining Bax degradation activity in a patient sample. The assay includes a labeled Bax protein which is incubated with a protein extract from the sample and a detector for detecting a signal from the labeled Bax protein, whereby decreased signals compared to a control indicates Bax degradation activity. Also provided by the present invention is a method for assaying a tissue for Bax degradation activity for determining aggressiveness of a tumor, for screening compounds for inhibitors of Bax degradation activity and for determining efficacy of proteasome inhibitors to prevent Bax degradation including the steps of incubating the sample with a labeled Bax protein and detecting the presence of a label generated signal whereby decrease signal compared to a control indicates Bax degradation activity. A method for screening potential proteasome inhibitors and anticancer drugs for efficacy in preventing Bax degradation activity. A method of determining tumor grade by measuring the Bax protein level and Bax degradation activity level whereby low or moderate levels of Bax protein and high levels of Bax degradation activity indicate a high–grade tumor is also provided.

17 Claims, 9 Drawing Sheets

(1 of 9 Drawing Sheet(s) Filed in Color)

OTHER PUBLICATIONS

Ciechanover A. "The ubiquitin–proteasome proteolytic pathway", *Cell* (1994), vol. 79, No. 1, pp. 13–21.

Ciechanover A. "The ubiquitin–proteasome pathway: on protein death and cell life", *EMBO J.* (1998), vol. 17, No. 24, pp. 7151–7160.

Corbett, T., et al., "In vivo methods for screening and preclinical testing: use of rodent solid tumors for drug discovery" in *Anticancer Drug Development Guide: Preclinical Screening, Clinical Trials and Approval*, Humana Press, Inc., Teicher, B.A. (ed.), 1997.

Cory, S. and Adams, J.M. "The Bcl–2 protein family: arbiters of cell survival", *Science* (1998), vol. 281, No. 5381, pp. 1322–1326.

Diehl, J.A., et al., "Inhibition of cyclin D1 phosphorylation on threonine–286 prevents its rapid degradation via the ubiquitin–proteasome pathway", *Genes Dev.* (1997), vol. 11, No. 8, pp. 957–972.

Dignam, J.D., et al., "Accurate transcription initiation by RNA polymerase II in a soluble extract from isolated mammalian nuclei", *Nucleic Acids Res.* (1983), vol. 11, No. 5, pp. 1475–1489.

Dimmeler, S., et al., "Dephosphorylation targets Bcl–2 for ubiquitin–dependent degradation: a link between the apoptosome and the proteasome pathway", *J Exp Med.* (1999), vol. 189, No. 11, pp. 1815–1822.

Dou, Q.P., et al., "Induction of a retinoblastoma phosphatase activity by anticancedr drugs accompanies p53–independent G1 arrest and apoptosis", *Proc Natl Acad Sci U S A.* (1995), vol. 92, No. 20, pp. 9019–9023.

Dou, Q.P., "Putative roles of retinoblastoma protein in apoptosis", *Apoptosis* (1997), vol. 2, pp. 5–8.

Dou, Q.P., et al., "Fas stimulation induces RB dephosphorylation and proteolysis that is blocked by inhibitors of the Ice protease family", *J Cell Biochem.* (1997), vol. 64, No. 4, pp. 586–594.

Dou, Q.P., et al., "Proteasome inhibition leads to significant reduction of Bcr–Abl expression and subsequent induction of apoptosis in K562 human chronic myelogenous leukemia cells", *J Pharmacol Exp Ther.* (1999), vol. 289, No. 2, pp. 781–790.

Dou, Q.P., and Li, B. "Proteasome inhibitors as potential novel anticancer agents", *Drug Resist Updat.* (1999), vol. 2, No. 4, pp. 215–223.

Dou, Q.P., et al., "Cyclin E and cyclin A as candidates for the restriction point protein", *Cancer Res.* (1993), vol. 53, No. 7, pp. 1493–1497.

Earnshaw, W.C. "Nuclear changes in Apoptosis", *Curr. Opin. Cell Biol.* (1995); vol. 7, pp. 337–343.

Evan, G. and Littlewood, T. "A matter of life and cell death", *Science* (1998), vol. 281, No. 5381, pp. 1317–1322.

Ezhevsky, S.A., et al., "Hypo–phosphorylation of the retinoblastoma protein (pRb) by cyclin D:Cdk4/6 complexes results in active pRb", *Proc Natl Acad Sci U.S.A.* (1997), vol. 94, No. 20, pp. 10699–10704.

Fang, G., et al., "Loop" domain is necessary for taxol–induced mobility shift and phosphorylatin of Bcl–2 as well as for inhibiting taxol–induced cytosolic accumulation of cytochrome c and apoptosis, *Cancer Res.* (1998), vol. 58, No. 15, pp. 3202–3208.

Fattman, C.L., et al., "Characterization of interior cleavage of retinoblastoma protein in apoptosis", *J Cell Biochem.* (1997), vol. 67, No. 3, pp. 399–408.

Fearnhead, H.O., et al., "Oncogene–dependent apoptosis is mediated by caspase–9", *Proc Natl Acad Sci U.S.A.* (1998), vol. 95, No. 23, pp. 13664–13669.

Fenteany, G., et al., "Inhibition of proteasome activities and subunit–specific amino–terminal threonine modification by lactacystin", *Science* (1995), vol. 268, No. 5211, pp. 726–731.

Fenteany, G., et al., "A beta–lactone related to lactacystin induces neurite outgrowth in a neuroblastoma cell line and inhibits cell cycle progression in an osteosarcoma cell line", *Proc Natl Acad Sci. U.S.A.* (1994), vol. 91, No. 8, pp. 3358–3362.

Fisher, D.E. "Apoptosis in cancer therapy: crossing the threshold", *Cell* (1994), vol. 78, No. 4, pp. 539–542.

Friess, H., et al., "bax, not bcl–2, influences the prognosis of human pancreatic cancer", *Gut* (1998), vol. 43, No. 3, pp. 414–421.

Goldberg, A.L. "Functions of the proteasome: the lysis at the end of the tunnel", *Science* (1995), vol. 268, No. 5210, pp. 522–3.

Gross, A., et al., "BCL–2 family members and the mitochondria in apoptosis", *Genes Dev.* (1999), vol. 13, No. 15, pp. 1899–1911.

Harima, Y., et al., "Bax and Bcl–2 expressions predict response to radiotherapy in human cervical cancer", *J Cancer Res Clin Oncol* (1998), vol. 124, No. 9, pp. 503–510.

Harper, M.E., et al., "Relationship of proliferating cell nuclear antigen (PCNA) in prostatic carcinomas to various clinical parameters", *Prostate* (1992), vol. 20, No. 3, pp. 243–253.

Harrington, E.A., et al., "Oncogenes and cell death", *Curr Opin Genet Dev.* (1994), vol. 4, No. 1, pp. 120–129.

Harrison, D.J. "Molecular mechanisms of drug resistance in tumours", *J Pathol.* (1995), vol. 175, No. 1, pp. 7–12.

Herrmann, J.L., et al., "Prostate carcinoma cell death resulting from inhibition of proteasome activity is independent of functional Bcl–2 and p53", *Oncogene* (1998), vol. 17, No. 22, pp. 2889–2899.

Hochstrasser M. "Ubiquitin, proteasomes, and the regulation of intracellular protein degradation", *Curr Opin Cell Biol.* (1995), vol. 7, No. 2, pp. 215–223.

Imajoh–Ohmi, S., et al., "Specific cleavage of the retinoblastoma protein by an ICE–like protease in apoptosis.", *EMBO J.* (1996), vol. 15, No. 24, pp. 6969–78.

Kayalar, C., et al., "Cleavage of actin by interleukin 1 beta–converting enzyme to reverse DNase I Inhibition.", *Proc Natl Acad Sci U.S.A.* (1996), vol. 93, No. 5, pp. 2234–2238.

Koshizuka, K., et al., "Combination therapy of a vitamin D3 analog and all–trans–retinoic acid: effect of human breast cancer in nude mice", *Anticancer Res.* (1999), vol. 19, No. 1A, pp. 519–524.

Krajewski, S., et al., "Reduced expression of proapoptotic gene BAX is associated with poor response rates to combination chemotherapy and shorter survival in women with metastatic breast adenocarcinoma", *Cancer Res.* (1995), vol. 55, No. 19, pp. 4471–4478.

Krajewski, S., et al., "Immunohistochemical determination of in vivo distribution of Bax, a dominant inhibitor of Bcl–2", *Am J Pathol.* (1994), vol. 145, No. 6, pp. 1323–1336.

Lamb, B.T., et al., "Introduction and expression of the 400 kilobase amyloid precursor protein gene in transgenic mice", *Nat Genet.* (1993), vol. 5, No. 1, pp. 22–30.

Lazebnik, Y.A., et al., "Cleavage of poly(ADP–ribose) polymerase by a proteinase with properties like ICE", *Nature* (1994), vol. 371, No. 6495, pp. 346–347.

Lee, S., et al., "Apoptosis and signal transduction: clues to a molecular mechanism", *Curr Opin Cell Biol.* (1993), vol. 5, No. 2, pp. 286–291.

Li, B. and Dou, Q.P. "Bax degradation by the ubiquitin/proteasome–dependent pathway: Involvement in tumor survival and progression", *Proc Natl Acad Sci U.S.A.* (2000), vol. 97, No. 8, pp. 3850–3855.

Li, B., et al., "Reciprocal expression of bcl–2 and p53 oncoproteins in urothelial dysplasia and carcinoma of the urinary bladder", *Urol Res.* (1998), vol. 26, No. 4, pp. 235–241.

Li, H., et al., "Cleavage of Bid by caspase 8 mediates the mitochondrial damage in the Fas pathway of apoptosis", *Cell* (1998), vol. 94, No. 4, pp. 491–501.

Linette, G.P., et al., "Cross talk between cell death and cell cycle progression: BCL–2 regulates NFAT–mediated activation", *Proc Natl Acad Sci U.S.A.* (1996), vol. 93, No. 18, pp. 9545–9552.

Loda, M., et al., "Increased proteasome–dependent degradation of the cyclin–dependent kinase inhibitor p27 in aggressive colorectal carcinomas", *Nat Med.* (1997), vol. 3, No. 2, pp. 231–234.

Lopes, U.G., et al., "p53–dependent induction of apoptosis by proteasome inhibitors", *J Biol Chem.* (1997), vol. 272, No. 20, pp. 12893–12896.

Mackey, T.J., et al., "bcl–2/bax ratio as a predictive marker for therapeutic response to radiotherapy in patients with prostate cancer", *Urology* (1998), vol. 52, No. 6, pp. 1085–1090.

Martin, S.J. and Green, D.R. "Protease activation during apoptosis: death by a thousand cuts?" *Cell* (1995), vol. 82, No. 3, pp. 349–352.

Martin, S.J., et al., "Cell–free reconstitution of Fas–, UV radiation–and ceramide–induced apoptosis", *EMBO J.* (1995), vol. 14, No. 21, pp. 5191–5200.

McPake, C.R., et al., "Bax is an important determinant of chemosensitivity in pediatric tumor cell lines independent of Bcl–2 expression and p53 status", *Oncol Res.* (1998), vol. 10, No. 5, pp. 235–244.

Milner, J., "DNA damage, p53 and cancer therapies", *Nat. Med.* (1995), vol. 1, pp. 789–880.

Miura, M., et al., "Induction of apoptosis in fibroblasts by IL–1 beta–converting enzyme, a mammalian homolog of the C. elegans cell death gene ced–3", *Cell* (1993), vol. 75, No. 4, pp. 653–660.

Molica, S., et al., "Increased bcl–2/bax ratio in B–cell chronic lymphocytic leukemia is associated with a progressive pattern of disease", *Haematologica* (1998), vol. 83, No. 12, pp. 1122–1124. (Abstract).

Numata, M., et al., "Identification of a mitochondrial Na+/H+ exchanger", *J Biol Chem.* (1998), vol. 273, No. 12, pp. 6951–6959.

Orlowski, R.Z., et al., "Tumor growth inhibition induced in a murine model of human Burkitt's lymphoma by a proteasome inhibitor", *Cancer Res.* (1998), vol. 58, No. 19, pp. 4342–4348.

Pagano, M., et al., "Role of the ubiquitin–proteasome pathway in regulating abundance of the cyclin–dependent kinase inhibitor p27", *Science* (1995), vol. 269, No. 5224, pp. 682–685.

Palombella, V.J., et al., "The ubiquitin–proteasome pathway is required for processing the NF–kappa B1 precursos protein and the activation of NF–kappa B", *Cell* (1994), vol. 78, No. 5, pp. 773–785.

Pepper, C., et al., "Elevated Bcl–2/Bax are a consistent feature of apoptosis resistance in B–cell chronic lymphocytic leukaemia and are correlated with in vivo chemoresistance", *Leuk Lymphoma* (1998) vol. 28, No. 3–4, pp. 355–361. (Abstract).

Plowman, J., et al., "Human tumor xenograft models in NCI drug development", in *Anticancer Drug Development Guide: Preclinical Screening, Clinical Trials, and Approval*, 1997, Humana Press, Inc., Totowa, NJ.

Portera–Cailliau, C., et al., "Apoptotic photoreceptor cell death in mouse models of retinitis pigmentosa", *Proc Natl Acad Sci U.S.A.* (1994), vol. 91, No. 3, pp. 974–978.

Reed, J.C. "Bcl–2 and the regulation of programmed cell death", *J Cell Biol.* (1994), vol. 124, No. 1–2, pp. 1–6.

Rock, K.L., et al., "Inhibitors of the proteasome block the degradation of most cell proteins and the generation of peptides presented on MHC class I molecules", *Cell* (1994), vol. 78, No. 5, pp. 761–771.

Shinohara, K., et al., "Apoptosis induction resulting from proteasome inhibition", *Biochem J.* (1996), vol. 317, Part 2, pp. 385–388.

Song, Q., et al., "DNA–dependent protein kinase catalytic subunit: a target for an ICE–like protease in apoptosis", *EMBO J.* (1996), vol. 15, No. 13, pp. 3238–3246.

Steller, H. "Mechanisms and genes of cellular suicide", *Science* (1995), vol. 267, No. 5203, pp. 1445–1449.

Strauss, W.M., et al., "Germ line transmission of a yeast artificial chromosome spanning the murine alpha 1(I) collagen locus", *Science* (1993), vol. 259, No. 5103, pp. 1904–1907.

Su, Z.Z., et al., "The cancer growth suppressor gene mda–7 selectively induces apoptosis in human breast cancer cells and inhibits tumor growth in nude mice", *Proc Natl Acad Sci U.S.A.* (1998), vol. 95, No. 24, pp. 14400–14405.

Sun, J., et al., "Both farnesyltransferase and geranylgeranyltransferase I Inhibitors are required for inhibition of oncogene K–Ras prenylation but each alone Is sufficient to suppress humor tumor growth in nude mouse xenografts", *Oncogene* (1998), vol. 16, No. 11, pp. 1467–1473.

Tai, Y.T., et al., "BAX protein expression and clinical outcome in epithelial ovarian cancer", *J Clin Oncol.* (1998) vol. 16, No. 8, pp. 2583–2590.

Tan, X., et al., "Degradation of retinoblastoma protein in tumor necrosis factor–and CD95–induced cell death", *J Biol Chem.* (1997), vol. 272, No. 15, pp. 9613–9616.

Thomas, A., et al., "Drug–induced apoptosis in B–cell chronic lymphocytic leukemia: relationship between p53 gene mutation and bcl–2/bax proteins in drug resistance", *Oncogene* (1996), vol. 12, No. 5, pp. 1055–1062.

Thornberry, N.A., and Lazebnik, Y. "Caspases: enemies within", *Science* (1998), vol. 281, No. 5381, pp. 1312–1316.

Tomoda, K., et al., "Degradation of the cyclin–dependent––kinase inhibitor p27Kip1 is instigated by Jab1", *Nature* (1999), vol. 398, No. 6723, pp. 160–165.

Tsujimoto, Y., et al., "Involvement of the bcl–2 gene in human follicular lymphoma", *Science* (1985), vol. 228, No. 4706, pp. 1440–1443. (Abstract).

Verma, I.M., et al., "Rel/NF–kappa B/I kappa B family: intimate tales of association and dissociation", *Genes Dev.* (1995), vol. 9, No. 22, pp. 2723–2735.

Vlach, J., et al., "Phosphorylation–dependent degradation of the cyclin–dependent kinase inhibitor p27", *EMBO J.* (1987), vol. 16, No. 17, pp. 5334–5344.

Wang, H.G. and Reed, J.C. "Mechanisms of Bcl–2 protein function", *Histol Histopathol.* (1998), vol. 13, No. 2, pp. 521–530.

Wang, T.T. and Phang, J.M. "Effects of estrogen on apoptotic pathways in human breast cancer cell line MCF–7", *Cancer Res.* (1995), vol. 55, No. 12, pp. 2487–2489.

Wang, X. and Zelenski, N.G., et al., "Cleavage of sterol regulatory element binding proteins (SREBPs) by CPP32 during apoptosis", *EMBO J.* (1996), vol. 15, No. 5, pp. 1012–1020.

White, E. "Regulation of Apoptosis by the Transforming Genes of the DNA Tumor Virus Adenovirus", *Proc. Soc. Exp. Biol. Med.* (1993), vol. 204, pp. 30–39.

Won, K.A. and Reed, S.I. "Activation of cyclin E/CDK2 is coupled to site–specific autophosphorylation and ubiquitin–dependent degradation of cyclin E", *EMBO J.* (1995), vol. 15, No. 16, pp. 4182–4193.

Wood, D.E., et al., "Bax cleavage is mediated by calpain during drug–induced apoptosis", *Oncogene* (1998), vol. 17, No. 9, pp. 1069–1078.

Wylie, A.H., et al., "Cell death: the significance of apoptosis", *Int Rev Cytol.* (1980), vol. 68, pp. 251–306.

Xiao, G., et al., "Suppression of breast cancer growth and metastatasis by a serpin myoepithelium–derived serine proteinase inhibitor expressed in the mammary myoepithelial cells", *Proc Natl Acad Sci U.S.A.* (1990), vol. 96, No. 7, pp. 3700–3705.

Burke and Olson, "Preparation of Clone Libraries in Yeast Artificial–Chromosome Vectors." *Methods in Enzymology*, vol. 194, "Guide to Yeast Genetics and Molecular Biology", eds. C. Guthrie and G. Fink, Academic Press, Inc., chap. 17:37–49.

Capecchi, "Altering the genome by homologous recombination" *Science*, 244:1288–1292 (1989).

Cregg JM, Vedvick TS, Raschke WC: Recent Advances in the Expression of Foreign Genes in *Pichia pastoris, Bio/Technology* 11:905–910, 1993.

Davies et al., "Targeted alterations in yeast artificial chromosomes for interspecies gene transfer", *Nucleic Acids Research*, vol. 20, No. 11, pp. 2693–2698 (1992).

Dickinson et al., "High frequency gene targeting using insertional vectors", *Human Molecular Genetics*, vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Gilboa, E, Eglitis, MA, Kantoff, PW, Anderson, WF: Transfer and expression of cloned genes using retroviral vectors. BioTechniques 4(6):504–512, 1986.

Green, D.R. and Reed, J.C. Mitochondria and Apoptosis. Science 1998;281: 1309–1312.

Hartwell, L.H, Kastan, M.B. Cell cycle control and cancer. Science 1994;266: 1821–1828.

Huston et al., 1991 "Protein engineering of single–chain Fv analogs and fusion proteins" in Methods in Enzymology (JJ Langone, ed,; Academic Press, New York, NY) 203:46–88.

Huxley et al., "The human HPRT gene on a yeast artificial chromosome in functional when transferred to mouse cells by cell fusion", *Genomics*, 9:742–750 (1991).

Jakobovits et al., "Germ–line transmission and expression of a human–derived yeast artificial chromosome", *Nature*, vol. 362, pp. 255–261 (1993).

Johnson and Bird, 1991 Construction of single–chain Fvb derivatives of monoclonal antibodies and their production in *Escherichia coli* in Methods in Enzymology (JJ Langone, ed.; Academic Press, New York, NY) 203:88–99.

Mernaugh and Mernaugh, 1995 "An overview of phage–displayed recombinant antibodies" in Molecular Methods in Plant Pathology (RP Singh and US Singh, eds.; CRC Press Inc., Boca Raton, FL) pp. 359–365.

Pearson and Choi, Expression of the human b–amyloid precursor protein gene from a yeast artificial chromosome in transgenic mice. Proc. Natl. Acad. Sci. USA, 1993. 90:10578–82.

Rothstein, "Targeting, disruption, replacement, and allele rescue: integrative DNA transformation in yeast" in *Methods in Enzymology*, vol. 194, "Guide to Yeast Genetics and Molecular Biology", eds. C. Guthrie and G. Fink, Academic Press, Inc., Chap. 19, pp. 281–301 (1991).

Schedl et al., "A yeast artificial chromosome covering the tyrosinase gene confers copy number–dependent expression in transgenic mice", *Nature*, vol. 362, pp. 258–261 (1993).

\* cited by examiner

Figure - 2a
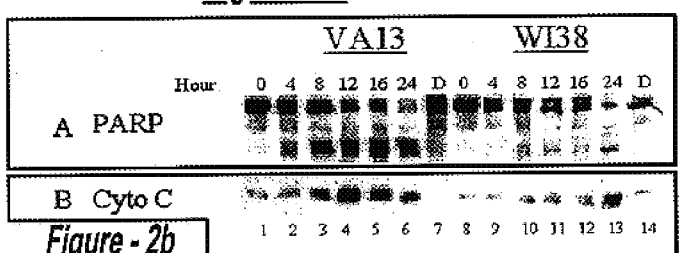
Figure - 2b
(included above)
Figure - 2c
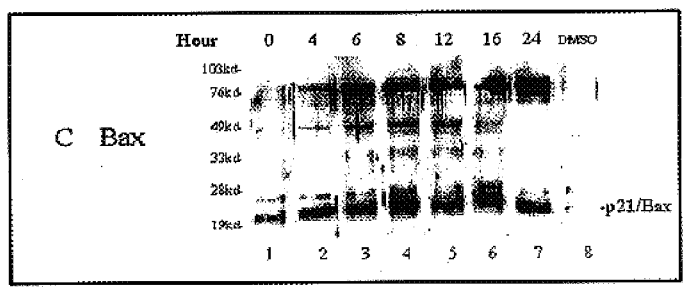
Figure - 2d
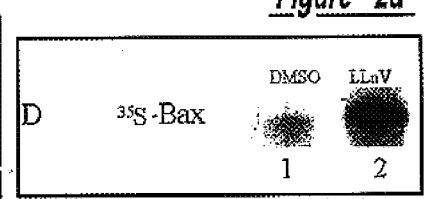
Figure - 2e
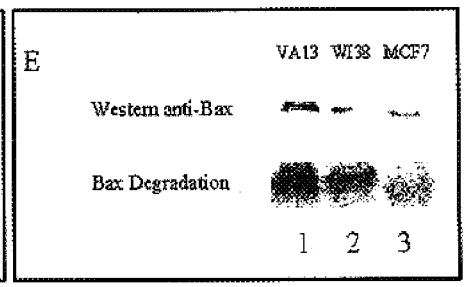

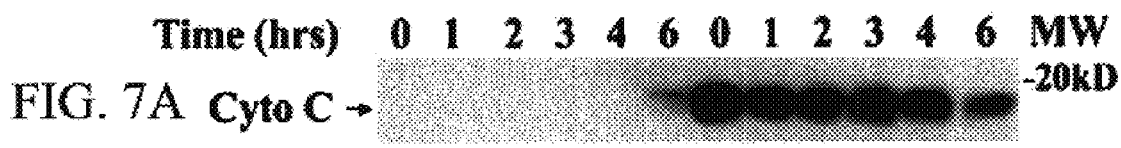
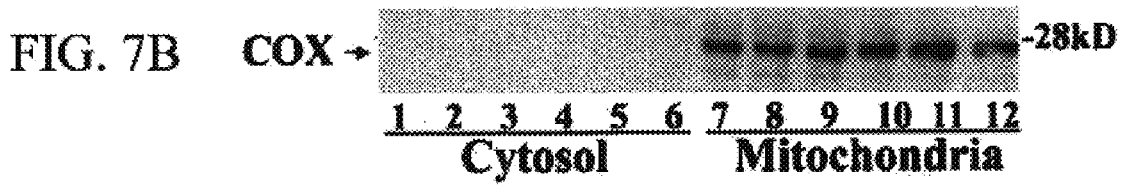
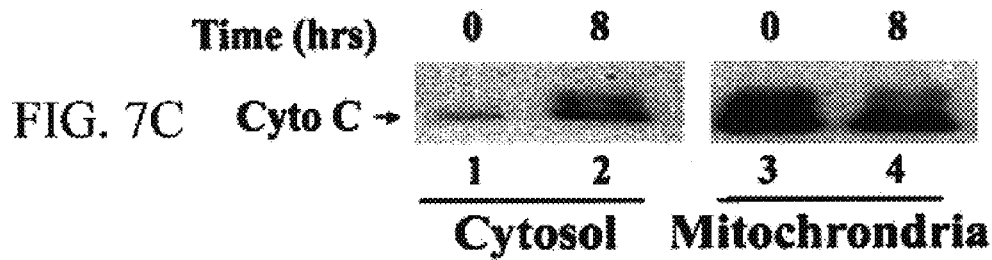
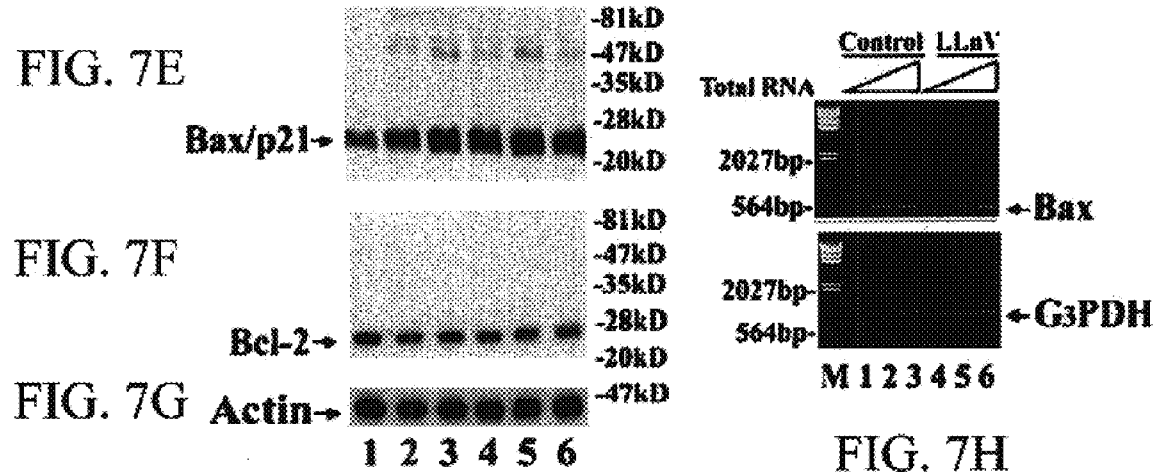
FIG. 7A – FIG. 7H

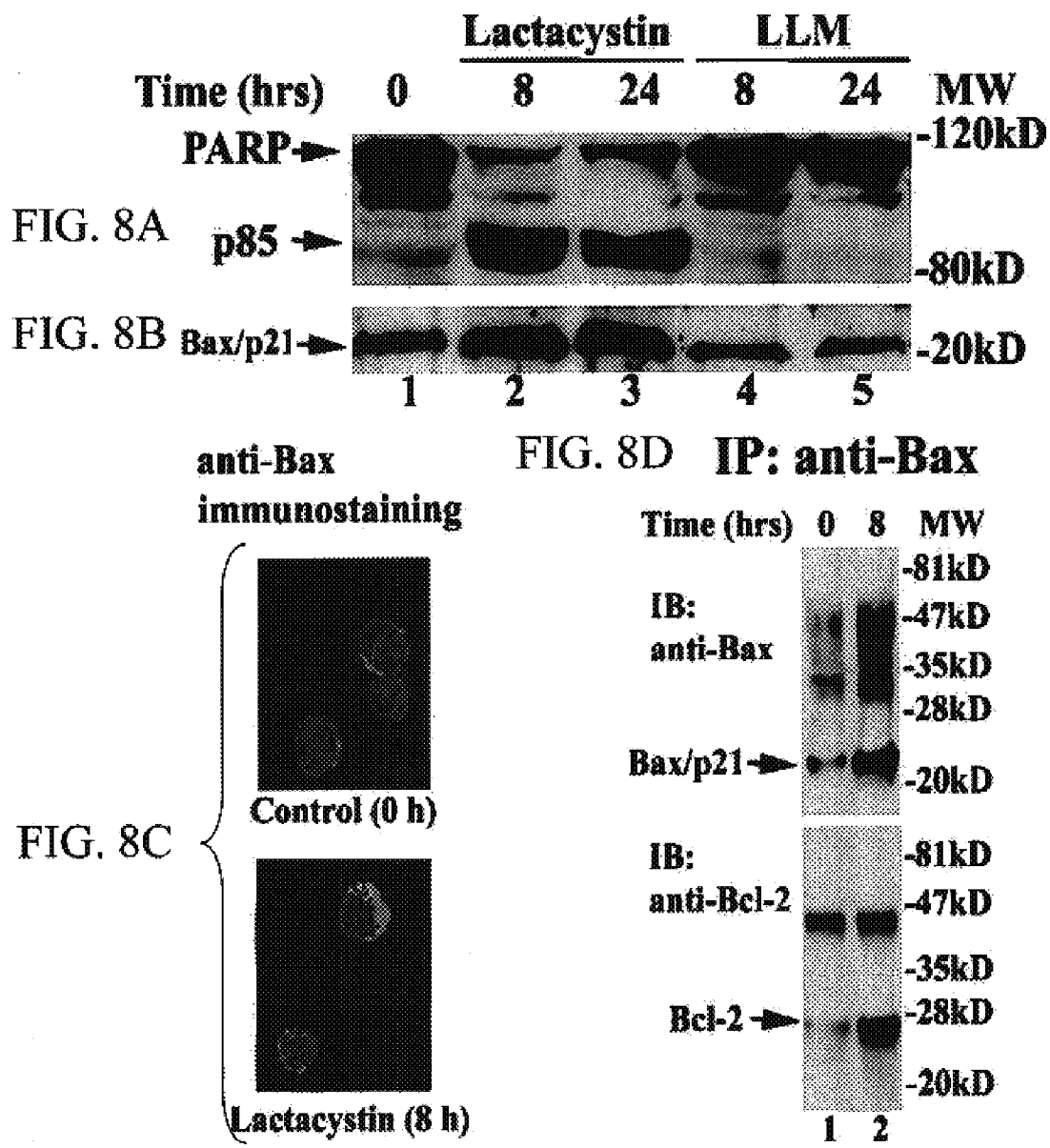

FIG. 9D

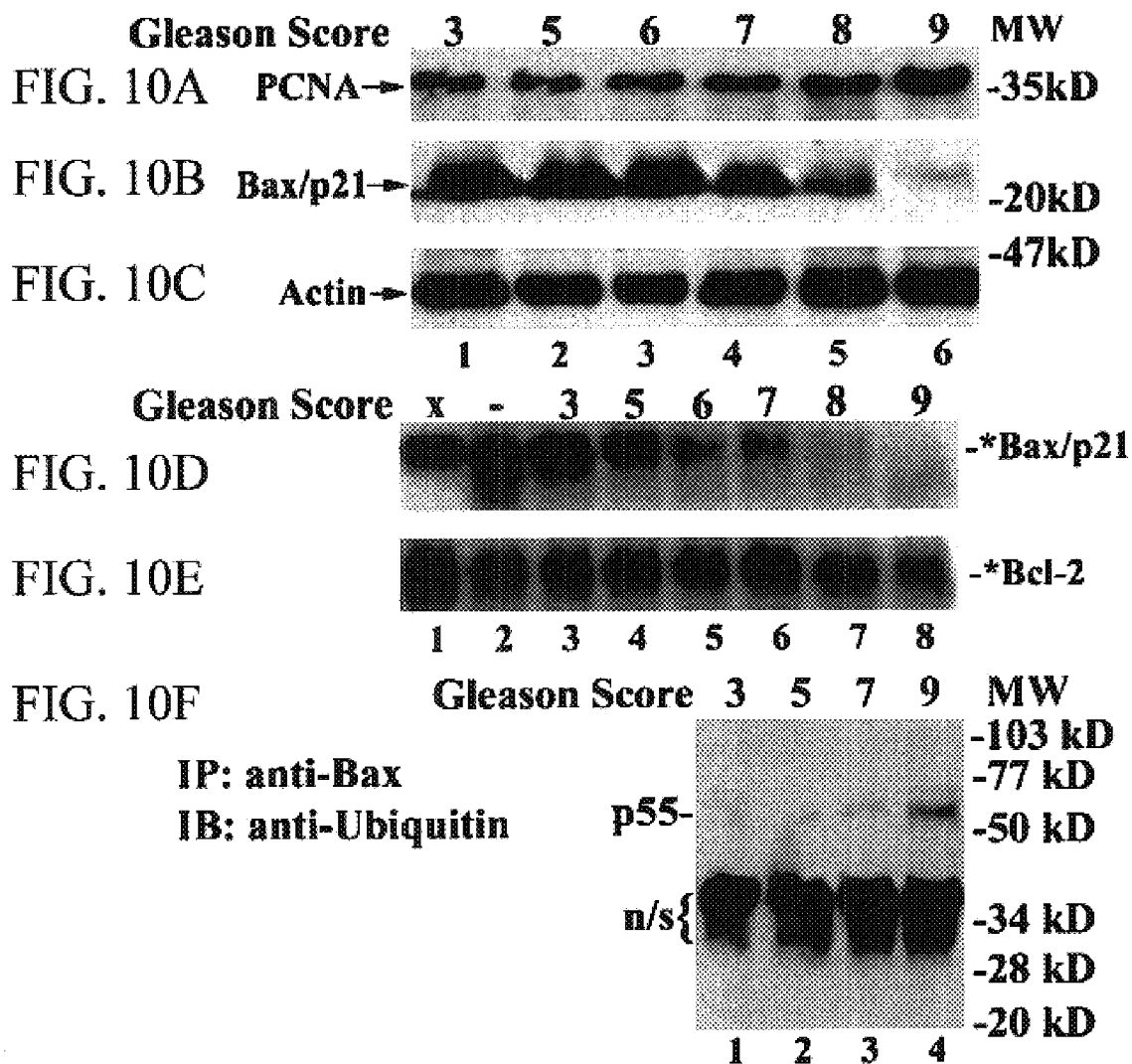

BAX DEGRADATION INVOLVEMENT IN TUMOR SURVIVAL AND PROGRESSION

CROSS REFERENCE TO RELATED APPLICATIONS

This application claims the benefit of priority under 35 U.S.C. Section 119(e) of U.S. Provisional Patent Application No. 60/186,895, filed Mar. 3, 2000, and U.S. Provisional Patent Application No. 60/217,264, filed Jul. 11, 2000, both of which are incorporated herein by reference.

BACKGROUND OF THE INVENTION

1. Field of the Invention

The present invention relates to assays for and treatment of tumors using Bax degradation activity. More specifically, the present invention relates to the using determinations of Bax degradation levels for prognosis and treatment of cancer.

2. Description of Related Art

Apoptosis, a morphologically distinct form of programmed cell death, plays a major role in development, homeostasis, and many diseases including cancer (Song and Steller, 1999). The process of apoptosis can be divided into three fundamental steps: initiation, commitment, and execution (Reed, 1997). The cell death pathway can be initiated by many stimuli and insults, including deprivation of growth factors or treatment with radiation, chemotherapeutic agents or the kinase inhibitor staurosporin (Reed, 1997).

The molecular mechanisms controlling apoptotic commitment are unclear. Results from the most recent experiments have suggested that cellular fate can be determined by Bcl-2 family proteins that are localized in mitochondria (Green and Reed, 1998; Adams and Cory, 1998; Gross et al., 1999). Apoptotic execution is initiated by activation of effector caspase protease (such as caspase-3) (Thornberry and Lazebnik, 1998), which in turn cleaves important cellular proteins, including a poly(ADP-ribose) polymerase (PARP) (Lazebnik et al., 1994), lamin (Lazebnik et al., 1995), DNA-dependent protein kinase (Song et al., 1996) and retinoblastoma protein (RB) (An and Dou, 1996); Tan et al., 1997). The active caspase-3 also cleaves a caspase-activated deoxyribonuclease inhibitor, resulting activation of the deoxyribonuclease that is responsible for the internucleosomal fragmentation of DNA (Enari et al., 1998), a hallmark of apoptotic execution (Thornberry and Lazebnik, 1998).

Several members of the Bcl-2 family (such as Bax, Bid and Bad) promote apoptosis, whereas the other Bcl-2 members (such as Bcl-2 and Bcl-XL) inhibit the cell death process (Green and Reed, 1998; Adams and Cory, 1998; Gross et al., 1999). The Bcl-2 family proteins also can form homodimers or heterodimers. The ratio of pro-apoptotic to antiapoptotic proteins in the Bcl-2 family is involved in determination of cellular fate (Green and Reed, 1998; Adams and Cory, 1998; Gross et al., 1999). In addition to their ratios, the mitochondrial localization of the Bcl-2 family proteins seems essential for their functions. It has been found that the pro-apoptotic Bcl-2 family members promote, while the antiapoptotic members block, the release of cytochrome c from mitochondria to the cytosol (Green and Reed, 1998; Adams and Cory, 1998; Gross et al., 1999). Once in cytosol, the released cytochrome c, together with Apaf-1, binds and activates caspase-9, which in turn cleaves and activates the effector caspase-3 (Li et al., 1997). The three-dimensional structures of Bcl-XL and Bid suggest that these proteins contain domains similar to the pore forming domains of some type of bacterial toxins (Chou et al., 1999). When added to synthetic membranes, Bcl-2, BclX$_L$ and Bax were able to form ion channels (Schlesinger et al., 1997; Minn et al., 1997). However, it is unclear whether Bcl-2 family proteins also modulate the pore formation in mitochondria in vivo to mediate cytochrome c release.

In the absence of a death signal, most of the anti- and pro-apoptotic Bcl-2 members are localized in separate subcellular compartments. While pro-apoptotic members mainly remain in cytosol, antiapoptotic members are localized on membranes of mitochondria, endoplasmic reticulum, and nucleus (Gross et al., 1999; Porter, 1999). Following a death signal, the pro-apoptotic members undergo a post-translational modification and/or a conformational change, followed by translocation to membranes of cellular compartments, especially mitochondria (Gross et al., 1999; Porter, 1999). For example, during tumor necrosis factor α- or Fas-induced apoptosis, Bid is first cleaved at its N-terminus by caspase-8, and the carboxy-terminal fragment of Bid is then inserted into the membrane of mitochondria (Li et al., 1998). In the presence of survival factors, bad is phosphorylated and sequestered in the cytosol by binding to 14-3-3 proteins. Following a death signal, Bad is dephosphorylated and then translocated to mitochondria where it interacts with, and inhibits, Bcl-X$_L$, or Bcl-2 (Zha et al., 1996). Upon apoptotic induction, Bax is also translocated to the mitochondria although the involved molecular mechanisms remain unclear. The Bax translocation process seems to involve its dimerization and conformational change (Gross et al., 1999), which is promoted by some unidentified cytosolic factors (Nmura et al., 1999). Moreover, removal of the amino-terminal 20 amino acids of Bax enabled it to target mitochondria in vitro in the absence of an activated cytosol (Goping et al., 1998). Finally, the Bid is able to induce the oligomerization and insertion of Bax into the outer mitochondrial membrane during apoptosis (Eskes et al., 2000).

The ubiquitin/proteasome system plays an important role in the degradation of cellular proteins. This proteolytic system includes two distinct steps: ubiquitination and degradation (Antonsson et al., 1997; Chang et al., 1998). Ubiquitination is the step after which the target protein can be selectively recognized by the proteasome complex from other proteins. Ubiquitination requires a reaction cascade. First, in an energy-dependent reaction, ubiquitin is activated by, and subsequently linked to, an Ubiquitin-Activating Enzyme (E1). Second, ubiquitin is passed on from E1 to Ubiquitin-Conjugating Enzymes (E2) and often subsequently to Ubiquitin Ligases (E3). Third, ubiquitin is then conjugated to the substrate protein, catalyzed by either E2 alone or a combination of E2 with E3. Usually, multiple ubiquitin molecules are added to the substrate by the same enzyme cascade. Degradation of such multi-ubiquitinated proteins occurs on a large 26S proteasome complex in an ATP-dependent manner. The 26S proteasome complex is composed of a 20S proteasome (the catalytic core) and a pair of 700 kDa-proteasome activators (the regulatory subunit) (Antonsson et al., 1997; Chang et al., 1998).

The ubiquitin/proteasome system is involved in the regulation of apoptosis. It has been found that proteasome inhibitors, such as tripeptide aldehydes (LLnL or LLnV; Dimmeler et al., 1999) or lactacystin (a microbial metabolite; Thomas et al., 1996), induce apoptosis in human leukemia (Krajewski et al., 1994; Mackey et al., 1998) and other cell lines. It has also been found that proteasome inhibitors are able to rapidly induce apoptosis in all the human cancer cell lines tested, including leukemia, breast, prostate, lung, bone, brain and head and neck, but not in human normal fibroblasts and normal breast cells. It was also reported that proteasome inhibition is sufficient to overcome apoptotic protection by Bcl-2 or Bcr-Abl oncoprotein. Therefore, the proteasome must selectively degrade one or more cellular proteins that play an important role in apoptotic commitment. However, nature of the responsible proteasome target protein(s) remains unknown.

Regulation of apoptosis is deranged in most, if not all, human cancers (Fisher et al, 1994). Many human cancers are resistant to induction of apoptosis (Fisher et al, 1994; Harrison et al., 1995; Milner et al., 1995) at least partially due to inactivation of the tumor suppressor protein p53 (Milner et al., 1995) or overexpression of the Bcl-2 (Reed et al., 1994) or Bcr-Abl oncoprotein (Bedi et al., 1994). Indeed, higher Bcl-2/Bax ratio correlates with poor therapeutic responsiveness to radio or chemotherapy in patients with prostate (Mackey et al., 1998) or B-cell chronic lymphocytic leukemia (Pepper et al., 1998). Even reduced expression of Bax alone is associated with poor response rates to radio or chemotherapy in patients with B-cell chronic lymphocytic leukemia (Molica et al., 1998), breast (Krajewski et al., 1995), ovarian (Tai et al., 1998), cervical (Harima et al., 1998) and pediatric cancers (McPake et al., 1998). In contrast, increased levels of Bax protein, or increased ratio of Bax/Bcl-2 protein, have been found to be tightly associated with increased therapeutic response (Tai et al., 1998; Harima et al., 1998). Furthermore, it has been suggested that Bax levels also influence the prognosis of human pancreatic cancer: patients whose tumors exhibited Bax immunostaining lived significantly longer (12 months) than those whose tumors were Bax negative (5 months) (Friess et al., 1998). What determines or regulates Bax levels in human cancer cells remains unknown.

Expression of oncogenes that deregulate cell proliferation can also induce apoptosis (White, 1993; Harrington et al., 1994), indicating that oncogene expression generates a proapoptotic signal that is present in transformed cells but absent in normal cells. Indeed, most recently, it has been found that an apoptosis-promoting complex consisting caspase-9, Apaf-1 and cytochrome c regulates the process of oncogene-dependent apoptosis (Fearnhead et al., 1998). Since caspase-9, Apaf-1 and cytochrome c are also present in normal cells, it is unclear what is the missing signal in normal cells that triggers activation of the apoptosis-promoting complex.

An assay to measure some aspect of Bcl2/Bax ratio in order to select patents that are most likely to benefit from radio- or chemotherapy protocols would be useful.

A method for measuring factors that regulate Bax levels in human cancer would be useful in evalutating the prognosis of a patient with cancer. It would also be useful to develop an assay or method for determining the efficacy of prospective chemotherapeutic agents for treating cancer via altering Bax levels.

SUMMARY OF THE INVENTION

According to the present invention, there is provided an assay for determining Bax degradation activity in a patient sample. The assay includes a labeled Bax protein which is incubated with a protein extract from the sample and a detector for detecting a signal from the labeled Bax protein, whereby decreased labeled signals compared to a control indicates Bax degradation activity. Also provided by the present invention is a method of assaying a sample for Bax degradation activity for determining aggressiveness of a tumor, for screening compounds for inhibitors of Bax degradation and for determining efficacy of protease inhibitors to prevent Bax degradation including the steps of incubating the sample with a labeled Bax protein and detecting the loss of the labeled Bax protein compared to a control indicates Bax degradation activity. A method of predicting tumor aggressiveness by measuring the Bax protein level and Bax degradation level whereby low or moderate levels of Bax protein and high levels of Bax degradation activity indicate a high-grade tumor is also provided

DESCRIPTION OF THE DRAWINGS

The file of this patent contains at least one drawing executed in color. Copies of this patent with color drawings will be provided by the Patent and Trademark Office upon request and payment of the necessary fee.

Other advantages of the present invention are readily appreciated as the same becomes better understood by reference to the following detailed description when considered in connection with the accompanying drawings wherein:

FIGS. 2A through 2E are photographs showing that proteasome inhibitor LLNV activates Bax and cytochrome c dependent apoptosis pathway;

FIGS. 7A–7H show proteasome inhibitor LLnV induces Bax accumulation, cytochrome c release and PARP cleavage in Bcl-2-overexpressing Jurkat T cells. (FIGS. 7A–7C) Jurkat T cells overexpressing Bcl-2 (0 h) were treated with 50 $\mu$M LLnV for up to 8 h, followed by preparation of cytosol and mitochondrial fractions. Both fractions were immunoblotted first by an antibody to cytochrome c (Cyto C, MW 17 kDa; FIG. 7A and FIG. 7C) and then reblotted by anti-cytochrome oxidase subunit II (COX, MW 26 kDa; FIG. 7B). Note: 20 $\mu$g protein from the cytosol, and 40 $\mu$g protein from the mitochondrial, preparation was used in each lane. (FIGS. 7D–7G) Whole cell extracts (70 $\mu$g per lane) of the above treated cells were immunoblotted with specific antibodies to PARP (FIG. 7D), Bax (clone N-20; FIG. E), Bcl-2 (FIG. 7F), or actin (FIG. 7G). Molecular masses of PARP, the PARP cleavage fragment (p85), Bax, Bcl-2 and actin are 113, 85, 21, 26 and 40 kDa, respectively. Positions of protein markers are indicated at right. (FIG. 7H) Bcl-2-expressing Jurkat cells (Control) were treated with 50 $\mu$M LLnV for 8 h, followed by RT-PCR. For the first-strand cDNA synthesis, 0.2 (lanes 1, 4), 0.6 (lanes 2, 5) and 1.8 $\mu$g (lanes 3, 6) of the total RNA were used. The positions of Bax (538 bp) and G$_3$PDH mRNA (983 bp) are indicated. Lane M is DNA molecular weight marker.

FIGS. 8A–8D show proteasome inhibition accumulates Bax to mitochondria/cytoplasm and increases interaction between Bax and Bcl-2 proteins. Jurkat cells (0 h; FIG. 8A and FIG. 8B) or Jurkat cells overexpressing Bcl-2 (0 h; FIG. 8C and FIG. 8D) were treated by either 10 µM lactacystin (FIGS. 8A–8C), 50 µM LLnV (FIG. 8D), or 50 µM LLM (FIG. 8A and FIG. 8B) for the indicated hours. (FIG. 8A and FIG. 8B) Western blotting with antibodies to PARP and Bax were performed as described in FIG. 7. (FIG. 8C) Immunohistochemistry (see MATERIALS AND METHODS). Localization of Bax protein (green) and nuclei (red) are shown. (FIG. 8D) Bax immunoprecipitates, prepared by an agarose-conjugated N-20 Bax antibody, were immunoblotted first with the 6A7 Bax antibody (upper) and then reblotted with a Bcl-2 antibody (lower).

FIGS. 9A–9F show Bax degradation depends on ubiquitination, proteasome and ATP. (FIG. 9A) Jurkat cells (0 h) were treated with either 50 µM LLnV or 10 µM lactacystin, followed by preparation of Bax immunoprecipitates (with clone 6A7), which were immunoblotted with an ubiquitin antibody. Positions of putative ubiquitinated Bax proteins (p47, p55) are indicated at left. The nature of the ~30 kDa and ~84 kDa remains unclear. (FIG. 9B) The [$^{35}$S]-labeled Bax (upper) or Bcl-2 (lower) protein (1 µl) were incubated at 37° C. for 2 h with either buffer Z only (lane 1) or 100 mg protein extract of MCF-7 cells grown exponentially (lane 2) or pretreated for 8 h with 50 mM LLnV (lane 3). (FIG. 9C) The [$^{35}$S]-labeled Bax protein (1 µl) was incubated with either buffer Z only (lane 1) or 100 µg MCF-7 cell lysate at 37° C. for 4 h, in the presence of an indicated inhibitor (100 mM; lanes 3–8) or an equal volume of DMSO (lane 2) in buffer Z. A weak band of ~16 kDa (indicated by an arrow) is probably an intermediate product of proteasome-mediated Bax degradation. (FIG. 9D) The proteasome in MCF-7 whole cell lysate (W lys, lane 1) was precipitated by using either ultraspin (ULS) or a proteasome subunit a6 antibody (IP). Both supernatant (lanes 2, 4) and pellet (lanes 3, 5) fractions were examined by Western blot assay using antibody to the proteasome a6 subunit (MW 33 kDa). (FIG. 9E) Bax degradation assay was performed as in FIG. 9B, with addition of buffer Z (lane 1) or 100 µg protein from MCF-7 whole cell lysate (lane 2), ultraspun supernatant (lane 3) or plus the pellet (lane 4), immunodepleted supernatant (lane 5) or plus a purified 20S proteasome (2 mg; lane 6), or the purified proteasome alone (2 µg; lane 7). (FIG. 9F) Bax degradation assay was performed as in FIG. 9B, in the absence (lane 3) or presence of 10 mM ATP (lane 2) or 10 mM ATP-y-S (lane 4).

FIGS. 10A–10F show the correlation of decreased Bax protein levels and increased Bax degradation in advanced human prostate cancer specimens (marked by increased Gleason Scores). (FIGS. 10A–C) Whole tissue extracts (100 µg/lane) were immunoblotted with specific antibodies to PCNA (MW 36 kDa; FIG. A), Bax (N-20; FIG. 10B) or Actin (FIG. 10C). (FIG. 10D and FIG. 10E) Bax or Bcl-2 degradation activity was assayed by incubating an [$^{35}$S]-labeled Bax or Bcl-2 protein (1 µl) with either buffer Z only (lane 1) or 200 µg protein extract prepared from either prostate adenocarcinomas with different grades (lanes 3–8) or a benign prostate hyperplasia (as a control; lane 2) at 37° C. for 4 h in buffer Z. (FIG. 10F) Whole tissue extracts (200 µg) were immunoprecipitated with 6A7 Bax antibody, followed by immunoblot with an ubiquitin antibody. Position of the putative ubiquitinated Bax, p55, is indicated. n/s indicates a possible non-specific band.

DESCRIPTION OF THE INVENTION

Generally, the present invention provides a method of Improving cancer diagnosis, prognosis and treatment More specifically, the present invention provides a method of determining Bax degradation by the ubiquitin/proteasome-dependent pathways, and establishing that Bax degradation is involved in tumor survival and progression. Bax degradation activity is useful as a prognostic indicator. Levels of Bax degradation activity also predicts response of tumor cells to proteasome inhibitor and other anticancer drugs whose activity is based on levels of Bax and Bax degradation activity. Accordingly, the present invention can be used for diagnosis, prevention and treatment of tumors.

By "tumors" as used herein, this term is intended to include, but is not limited to breast tumors, prostate tumors, leukemia, lung, cervical, head and neck cancer, and other tumors known to those of skill in the art to have Bax activity.

By "labels" as used herein, the term is intended to include, but is not limited to, chemoluminescent labels, fluorescent labels, radiolabels, enzymatic labels and other such labels known to those of skill in the art to be useful in assays.

By "patient sample" as used herein the term is intended to include any type of sample which can contain tumor samples. This list therefore includes, but is not limited to, tissues, washing, excretions, fluids including saliva, blood, urine, tears, sweat, secretions, and other samples known to those of skill in the art in include tumor samples.

It has been determined that Bax is mainly regulated by the ATP-, ubiquitin- and proteasome-dependent degradation pathway. Further, there has been determined a relationship between Bax degradation activity and cancer progression. Therefore, increased levels of Bax ubiquitination and degradation correlates with decreased levels of Bax protein as well as progression of human prostate cancer.

The ubiquitin/proteasome system plays an important role in the degradation of cellular proteins that are involved in regulating different cellular processes including apoptosis (Hochstrasser, 1995; Dou et al., 1999). It is reported herein that Bax is a direct target protein of the ubiquitin/proteasome pathway. Inhibition of this pathway by a proteasome inhibitor in Bcl-2-overexpressing Jurkat T cells resulted in accumulation of Bax and its ubiquitinated forms, but had no effect on Bax mRNA level. The increased Bax-immunofluorescent signals were primarily localized to mitochondria/cytoplasm, and associated with increased levels of Bax-Bcl-2 interaction. This was followed by the mitochondrial cytochrome c release and the caspase activation. Furthermore, correlated to decreased Bax expression, levels of Bax degradation were significantly increased in aggressive prostate cancer tissue samples.

Figure 3:
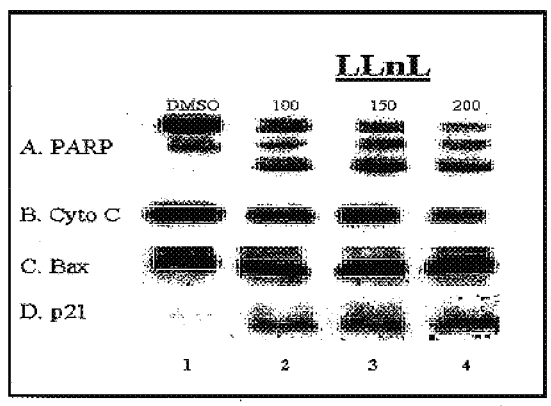
FIG. 3 is a photograph showing proteasome inhibitor LLNL at high concentration induces Bax and cytochrome c independent apoptosis in normal WI-38 cells.

Previously, it was reported that proteasome inhibitors were able to induce apoptosis in human Jurkat cells overexpressing Bcl-2 protein (An et al., 1998). Another group also reported a similar finding using Bcl-2-overexpressing prostate cancer cells (Herrmann et al., 1998). In the current study, the molecular basis for the ability of proteasome inhibitors to overcome Bcl-2 antiapoptotic function was investigated. It was demonstrated that Bax, an inhibitor of Bcl-2, is a direct target of the proteasome (FIGS. 1–3). This shows that Bax accumulation by proteasome inhibition is associated with the proteasome inhibitor's ability to overcome the Bcl-2 protective function. First, Bax protein levels were increased prior to release of cytochrome c from mitochondria to the cytosol (FIG. 1, E vs. A, C). Second, Bax was primarily accumulated in cytoplasm during proteasome inhibition; the observation that the increased Bax signals clustered around nuclei suggests accumulation in mitochondria (FIG. 2C). Third, proteasome inhibition-accumulated Bax protein was able to interact with Bcl-2 (FIG. 2D). Finally, Bcl-2 protein levels remained relatively unchanged during proteasome inhibition (FIG. 1F).

Compared to cell-free Bax degradation, no or much less Bcl-2 proteolysis was observed after incubation with a tumor cell or tissue extract (FIG. 3B, lower vs. upper; FIG. 4E vs. 4D). In addition, the tumor suppressor p53, another target of the ubiquitin/proteasome pathway (Hochstrasser, 1995; Dou et al., 1999), was much more resistant than Bax to induction of cell-free degradation (Li, B., Peng, Y., Chen, J. and Dou, Q. P., unpublished data). It seems that the in vitro degradation assay preferably detects degradation of Bax over Bcl-2 and p53.

Figure 4:
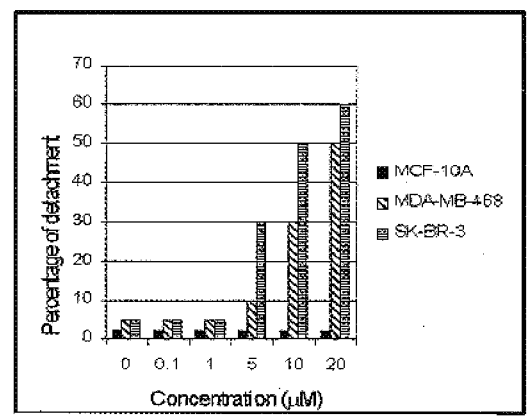
FIG. 4 is a graph showing lactacystin selectively induces detachment in apoptosis in human breast cancer versus normal cells.

In the present application, it was also reported that decreased Bax levels correlated well with increased Bax degradation in aggressive prostate tumor samples, whereas no such correlation was found between levels of Bcl-2 protein or Bcl-2 degradation activity and Gleason Scores of these tumor samples (Table 1 and FIG. 4). Furthermore, all high-grade tumors expressed low/moderate levels of Bax protein and high levels of Bax degradation activity, whereas most of low- and mid-grade tumors contained high levels of Bax protein and low/moderate levels of Bax degradation activity. It should be noted that two previous studies using immunohistochemical assay showed that Bax levels did not correlate with Gleason grade of prostate cancer (Krajewski et al., 1994; Mackey et al., 1998).

The data shows that Bax degradation is an important regulatory mechanism for controlling Bax protein levels, which plays an important role in advancing prostate cancer. Discovery of the correlation between proteasome-mediated Bax degradation and prostate cancer progression has great clinical significance in diagnosis, treatment and prognosis of human prostate and other cancers.

Also provided by the present invention is a cell free Bax degradation assay, method of using the assay and kit containing therein the materials needed for the assay. This assay is useful for determining the Bax levels, particularly in cancer cells, which can further predict differential responses to chemotherapy and/or radiation therapy. This is also useful in determining a prognosis of a patient's disease, for example in prostate cancer. The assay is also useful as a method of drug screening to find compounds that interact with Bax and the related pathway. For example, a cell-free Bax degradation assay was established in which as in vitro-translated [$^{35}$S]-labeled Bax protein can be degraded by a tumor cell protein extract. For example, but not limited to, a cell-free Bax degradation activity assay was established in which an in vitro-translated radiolabeled Bax protein is incubated with a tumor cell protein extract and Bax degradation activity is measured.

Furthermore, a fast screen assay for proteasome inhibitors was developed. Briefly, whole cell extracts were prepared from growing human Jurkat T cells, which contain high levels of the chymotrypsin-like activity of the proteasome. Protein extract was mixed with fluorogenic proteasome peptide substrate and 5 microM of a candidate proteasome inhibitor of the authentic peptide proteasome inhibitor LLL (as a control). Measurement of peptide substrate after incubation indicates efficacy of proteasome inhibitors.

By performing this assay, multiple compounds can be screened, and compounds can be obtained that exhibit potent proteasome inhibitory activity (80–93% inhibition at 5 microM) equivalent to the potency of LLL.

The ability of these compounds to inhibit the proteasome in tumor cells and the ability of these compounds to induce tumor growth arrest or cell death/apoptosis was measured.

For example, but not limited to, human cell lines overexpressing Bcl-2 protein or Bcl-Abl oncogene were incubated with selected putative proteasome inhibitors of LLL (as a control), followed by incubation with a peptide substrate. Peptide substrate products and the accumulation of natural proteasome target proteins (i.e. p27, p21, and Bax) were measured. This was done using HL-60, Jurkat T, K562 (overexpressing Bcl-Abl oncogene) and Jurkat T cells overexpressing Bcl-2 protein, for these in vivo studies.

To measure inhibition of the proteasome activity in vivo, tumor cells, cultured in 24-well plates, are first incubated for 12 hours with various concentrations of the selected putative proteasome inhibitors or LLL (as a control), followed by an additional 2 hour-incubation with a fluorogenic peptide substrate. After that, cell medium (200 microl) is collected and used for measurement of free AMCs. The accumulation of natural proteasome target proteins (i.e., p27, p21 and Bax) and their ubiquitinated forms is also measured.

A detailed description of the Bax degradation activity assay and screening assay for proteasome inhibitors is set forth in the following non-limiting examples and accompanying Figures, included herewith and incorporated by reference in its entirety.

EXAMPLES

Example 1

Materials and Methods

Materials: Tripeptidyl protease inhibitors, phosphocreatinine, creatine phosphokinase, ATP, ATP-gamma-S, ubiquitin and other chemicals were purchased from Sigma (St. Louis, Mo.). Purified 20S proteasome, lactacystin and clasto-lactacyctin b-lactone (b-lactone) were from Calbiochem (La Jolla, Calif.). Stocks of proteasome and protease inhibitors were prepared in DMSO as described (Dou et al., 1999). Purified mouse monoclonal antibodies to human Bax (clone 6A7) and PCNA (clone PC-10) were purchased from Santa Cruz Biotech (Santa Cruz, Calif.); to human Bcl-2 (clone 2–124) from Dako (Glostrup, Denmark); to human cytochrome c (clone 7H8.2C12) from Pharmingen (San Diego, Calif.); to cytochrome oxidase subunit II (clone 12c4-f12) from Molecular Probes (Eugene, Oreg.); to 20S proteasome subunit a6 (clone HC2) from Affiniti Research Products (Exeter, UK). Rabbit polyclonal antibody to human PARP was from Boehringer Manheim (Indianapolis, Ind.); to human Bax (clone N-20) and actin (clone C11) from Santa Cruz Biotech.; to human ubiquitin from Sigma.

Cell Culture and Drug Treatment: Human breast cancer MCF-7 cells, Jurkat T cells, and Jurkat T cells stably transfected with pRcCMV vector containing a complete human bcl-2 cDNA (obtained from Dr. Hong-gang Wang, Moffitt Cancer Center & Research Institute) were grown in RPMI 1640 growth medium (An et al., 1998). Treatment of cell with a proteasome inhibitor was performed as described (An et al., 1998; Dou et al., 1999).

Western blot analysis and Immunoprecipitation: Whole cell extract (An et al., 1996), whole tissue extracts (Loda et al., 1997), and cytosol and mitochondria fractions (Fang et al., 1998) were prepared as described. The enhanced chemiluminescence Western blot assay was performed as described previously (An et al., 1996). To perform a coupled immunoprecipitation-Western blot assay, a whole cell or tissue extract (200 microg protein) was first precleared by incubating with protein A plus protein G agarose beads (Calbiochem) at 4° C. for 2 hours. The collected supernatant was then incubated for at least 3 hours with either 10 ml of agarose beads conjugated with the N20 Bax antibody (Santa Cruz Biotech), or the 6A7 Bax antibody, followed by incubation with protein A/protein G beads at 4° C. overnight. The washed Bax immunoprecipitates were boiled in SDS sample buffer and used for Western blotting with antibodies to Bax, Bcl-2 or ubiquitin.

In vitro Bax Degradation Assay: Human Bax-a cDNA subcloned into pcDNA$_3$ was a gift from Dr. Hong-gang Wang. Human full length of bcl-2-a cDNA was cloned from Jurkat T cells and subcloned into pcDNA3.1(−) as described+. Both bax and bcl-2 plasmids were used for coupled in vitro transcription/translation (Promega; Madison, Wis.) in the presence of [$^{35}$S]methionine (Amersham Pharmacia Biotech; Piscataway, N.J.). Protein extracts were prepared from either MCF-7 cells or prostate tumor tissues in buffer Y (50 mM Tris-HCl, pH 7.4, 250 mM NaCl, 1% Triton X-100, 0.1% SDS, 1 mM EDTA), and used for Bax (or Bcl-2) degradation assay. Briefly, 1 microl of [$^{35}$S]-labeled Bax (or Bcl-2) protein was incubated at 37° C. for 2–4 hours with 100–200 microg protein extract in buffer Z (50 mM Tris-HCl, pH 7.4, 5 mM MgCl$_2$, 3 mM DTT, 10 mM ATP, 10 mM phosphocreatine, 10 microg/ml creatine phosphokinase, 10 microg/ml aprotinin, 10 microg/ml leupeptin, 10% glycerol and 2 microg/ml ubiquitin). After incubation, the samples were subjected to gel electrophoresis and autoradiography. Under the cell-free assay conditions, the calpain-mediated Bax cleavage activity was blocked by omission of calcium and addition of the protease inhibitor leupeptin (Wood et al, 1998). To deplete the proteasome, MCF-7 cell lysates were either immunoprecipitated with the 20S proteasome subunit a6 antibody or ultracentrifugated at 100,000×g for 6 hours. The proteasome-enriched pellet fraction was resuspended in buffer Y.

EXAMPLES

Immunocytochemistry and Reverse Transcriptase-Polymerase Chain Reaction (RT-PCR): Immunocytochemistry was performed with the rabbit polyclonal Bax antibody (N20) and an FITO-labeled goat anti-rabbit antibody (Southern Biotech.; Birmingham, Ala.), followed by counter-staining nuclei with propidium iodide (Sigma) (Bossy-Wetzel et al., 1998). To perform RT-PCR, total RNA was isolated from Jurkat T cells by an Advantage RT-for-PCR kit (Clontech; palo Alto, Calif.). The primer pairs used for amplification of BAX mRNA (538 bp) were forward (SEQ. ID. NO. 1) 5'CAGXTXTGAGATCATGAAGACA-3' and reverse (SEQ. ID. NO. 2) 5'-GCCCATCTTCTTCCAGATGGTGAGC-3' (Wang et al, 1995). PCR was conducted by using a MasterTaq DNA polymerase kit (Eppendorf Scientific; Westbury, N.Y.), followed by agarose gel analysis. All results were normalized to G$_3$PDH mRNA (983 bp; Clontech).

Results

Proteasome inhibitors are able to accumulate Bax protein and subsequently induce cytochrome c-dependent apoptosis in Jurkat T cells overexpressing Bcl-2 protein. It was first determined whether cytochrome c release is associated with proteasome inhibition-induced apoptosis in Bcl-2 expressing cells. Treatment of Bcl-2-overexpressing Jurkat cells with the tripeptidyl proteasome inhibitor LLnV for 6 to 8 hours increased the level of cytosolic cytochrome c, accompanied by a decrease in the level of the mitochondrial cytochrome c (FIG. 7A and FIG. 7C). The increased cytosolic cytochrome c was not due to a contamination from the mitochondria preparation because expression of cytochrome oxidase (COX), an enzyme that is localized in mitochondria (Barrell et al., 1979), was detected only in the membrane-bound, but not the cytosolic, fraction (FIG. 7B). Release of cytochrome c in LLnV-treated Bcl-2 cells was associated with induction of apoptosis, as demonstrated by cleavage of PARP (FIG. 7D). This data suggests that proteasome inhibition-induced apoptosis in Bcl-2-overexpressing cells is associated with cytochrome c release.

To show that Bax is a direct target protein of the ubiquitin/proteasome pathway, Bax protein levels were measured in the same experiment by Western blot assay. The level of Bax protein (Bax/p21) was increased after LLnV treatment for 1 hour or longer (FIG. 7E). In contrast, Bax mRNA level remained unchanged during proteasome inhibition (FIG. 7H). The LLnV treatment also increased levels of several Bax-related, high molecular weight polypeptides (FIG. 7E; also see FIG. 8D, upper), suggesting Bax posttranslational modification. Little changes were observed in levels of the overexpressed Bcl-2 protein in these cells (FIG. 7F). Therefore, LLnV treatment of Bcl-2 expressing cells increased the Bax protein level and the Bax/Bcl-2 ration, which is associated with the ability of this proteasome inhibitor to overcome Bcl-2-mediation protection from apoptosis.

Figure 5A:
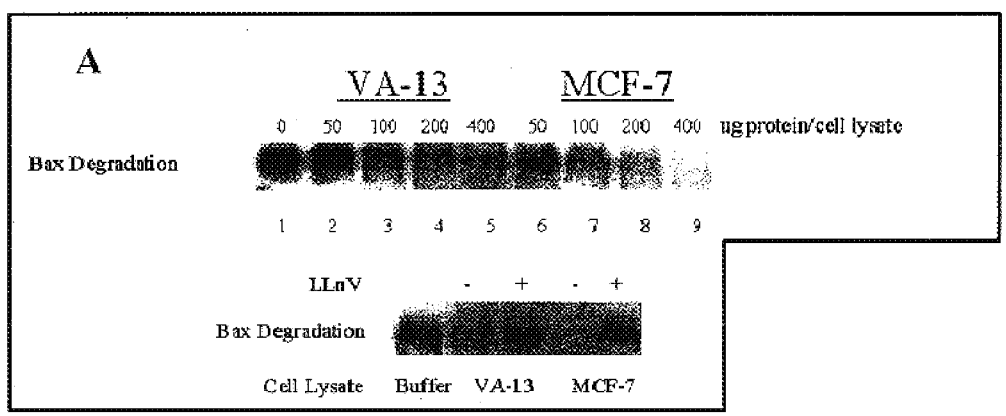
FIGS. 5A and 5B are photographs showing BDA levels predicts both Bax levels and cancer cell sensitivity to proteasome inhibitor induced apoptosis.
Figure 5B:
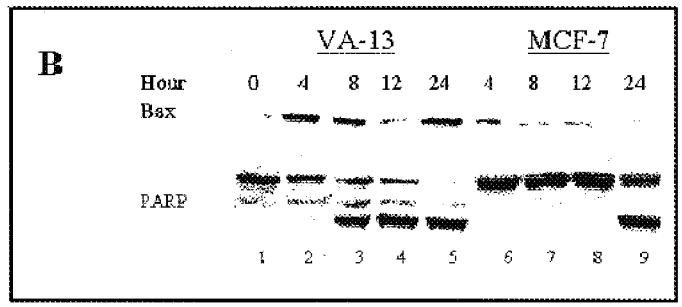

LLnV inhibits not only the proteasome activity but also some cysteine proteases, such as calpain and cathepsin B (Rock et al., 1994). To confirm that Bax accumulation and subsequent apoptosis induction are due to inhibition of the proteasome activity, a specific proteasome inhibitor (Fenteany et al., 1995), lactacystin, and LLM, a strong inhibitor of calpain and cathepsin but a very weak inhibitor of the proteasome (Rocket al., 1994), were used. Treatment of Jurkat T cells with 10 microM lactacystin induced Bax accumulation and PARP cleavage (FIG. 5B and FIG. 8A, lanes 1–3). In contrast, LLM at 50 microM had no such effects (FIG. 5B and FIG. 5A, lanes 4, 5, vs. 1). Therefore, inhibition of the proteasome, but not a cysteine protease, pathway results in Bax accumulation and apoptosis induction.

Cellular localization of Bax protein accumulated was determined by a proteasome inhibitor by immunofluorescent staining. In untreated Bcl-2-overexpressing Jurkat cells, Bax protein was primarily expressed in the cytoplasm (FIG. 5C, upper). Treatment with LLnV or lactacystin (FIG. 5C, upper). Treatment with LLnV or lactacystin (FIG. 8C, lower) markedly increased the cytoplasmic Bax-immunofluorescent signals, which was consistent with the results obtained from Western blotting (FIG. 7E and FIG. 5B). The increased Bax signals remained largely in clusters in cytoplasm around nuclei (FIG. 5C), suggesting accumulation of Bax protein in mitochondria.

In order to determine the functional significance of proteasome inhibition-accumulated Bax protein in Bcl-2-overexpressing cells, the interaction between Bax and Bcl-2 proteins was measured by a coupled immunoprecipitation-Western blot assay. Bax immunoprecipitates were prepared from untreated and LLnV-treated Bcl-2-expressing cells using a polyclonal Bax antibody, followed by immunoblot with monoclonal antibodies to Bax and Bcl-2, respectively (FIG. 5D, upper and lower, respectively). LLnV treatment significantly increased levels of both Bax/p21 and the Bax-bound Bcl-2 protein (FIG. 5D, upper and lower). The nature of a band of ~46 kDa, detected by the Bcl-2 antibody in Bax immunoprecipitates (FIG. 5D, lower), remains unknown. LLnV also dramatically increased levels of multiple bands in a range of 30 to 60 kDa, most of which were detected by the antibody to Bax, but not to Bcl-2 (FIG. 8D, upper vs. lower), indicating that most of them contain only Bax protein (also see FIG. 9A). The data demonstrates that proteasome inhibitor-accumulated Bax protein is able to interact with Bcl-2, which correlates to release of mitochondrial cytochrome c and inhibition of the Bcl-2 antiapoptotic function.

Bax Degradation is Dependent on Ubiquitin, Proteasome and ATP.

Figure 9A:
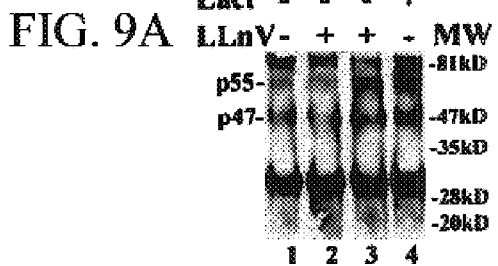

If Bax is a direct target of the ubiquitin/proteasome pathway, inhibition of the proteasome activity should accumulate ubiquitinated forms of Bax protein. To investigate this possibility, protein extracts of Jurkat T cells treated with lactacystin or LLnV were immunoprecipitated with a monoclonal Bax antibody, followed by Western blot assay using a polyclonal ubiquitin antibody. Several polypeptide bands including a p55 and a p47 were detected in the untreated cell lysate (FIG. 9A, lane 1). Treatment with lactacystin for 4 hours, or with LLnV for 8 hours, significantly increased both p55 and p47 levels (FIG. 9A), suggesting that they are probably poly-ubiquitinated forms of Bax.

Figure 9B:
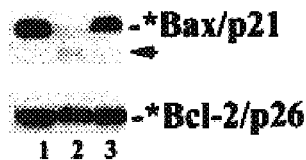
Figure 9C:
Figure 9E:
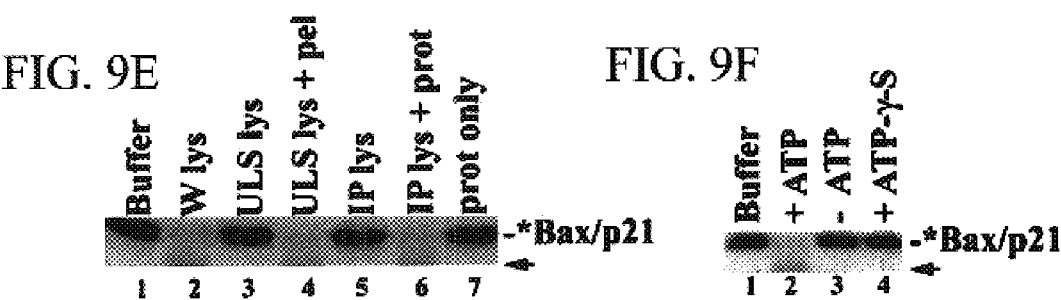

To further study the proteasome activity that degrades Bax protein, a cell-free Bax degradation assay was developed by using an in vitro-translated, [$^{35}$S]-labeled Bax protein as substrate (FIG. 9B, upper, lane 1). The Bax degradation activity is present in protein extracts prepared from exponentially growing MCF-7 (FIG. 9), K562, VA-13, WI-38, Jurkat T or HL-60 cells. The labeled Bax was almost completely degraded by a MCF-7 cell extract after 2 to 4 hours incubation at 37° C. (FIG. 9B, upper, and FIG. 9C, lanes 2 vs. 1). In contrast, no or little decrease in the level of a labeled Bcl-2 was detected after in vitro incubation (FIG. 9B, lower, lanes 2 vs. 1). When MCF-7 cells were pretreated with the proteasome inhibitor LLnV, the cell-free Bax degradation activity was inhibited (FIG. 9B, lanes 3 vs. 2). The Bax degradation process was also blocked by a 10-minute preincubation of the cell extract with the tripeptide proteasome inhibitor LLL, LLnV or LLnL, but not with the tripeptide cysteine protease inhibitor LLM (FIG. 9C, lanes 5–8 vs. 2). In addition, Bax degradation activity was blocked by b-lactone (Lactone), the active product of lactacystin (Fenteany et al, 1994), but not by lactacystin itself (Lact) (FIG. 9C, lanes 3, 4 vs. 2), suggesting failure of lactacystin to covert to b-lactone under the cell-free conditions. However, Bax degradation activity was not inhibited by several other protease inhibitors, including leupeptin, aprotinin, N-ethylmaleimide, phenylmethylsulfonyl fluoride, benzamidine, tosyl-L-lysine chloromethyl ketone, acetyl-YVAD-chloromethyl ketone, and acetyl-DEVD-fluoromethyl ketone. The effects of proteasome depletion on the cell-free Bax degradation (FIG. 9D and FIG. 9E) were determined. An ultracentrifugation of the MCF-7 whole cell lysate (W lys) resulted in precipitation of the proteasome (ULS pel), as judged by Western blot assay using a specific antibody to the proteasome subunit a6 (FIG. 9D, lanes 1–3). The proteasome-depleted supernatant (ULS lys) had also lost its Bax degradation activity, which was reconstituted by addition of the pellet fraction (pel) (FIG. 9E, lanes 2–4). The proteasome complex in the MCF-7 cell lysate was also successfully immunodepleted by using the proteasome a6 antibody (FIG. 9D, lanes 4, 5), associated with loss of Bax degradation activity, which could be recovered by addition of a purified 20S proteasome (prot) (FIG. 9E, lanes 5, 6). Addition of the purified proteasome alone was not sufficient to degrade Bax protein (lane 7), which is consistent with the idea that Bax ubiquitination is required for its degradation.

Figure 9F:
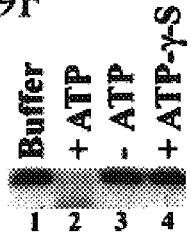

The cell-free Bax degradation assay was performed in the presence of ATP, suggesting requirement for ATP. Indeed, Bax was not degraded if ATP was omitted or replaced by ATP-gamma-S, a non-hydrolyzable analog of ATP (FIG. 9F, lanes 3, 4 vs. 2). Taken together, both in vivo and in vitro studies have demonstrated that Bax is regulated by an ATP- and ubiquitin-dependent, proteasome-mediated degradation pathway.

Decreased levels of Bax protein correlate with increased levels of Bax degradation in advanced human prostate cancer. If constant degradation of the apoptosis inducer Bax by the proteasome is a cancer cell survival mechanism, the levels of Bax degradation activity should be increased in aggressive cancers. Bax protein expression and Bax degradation activity were analyzed in frozen specimens of prostate adenocarcinomas. 38 cases of prostate tumor samples were obtained, which include 22 cases with Gleason Scores 3–6 (low grade), 10 cases with Gleason Score 7 (moderate), and 6 cases with Gleason Scores 8–10 (high grade). In a selected subset of tumor samples (16 cases; Table 1 and FIG. 10), progression to prostate cancer (marked by increased Gleason Scores) was confirmed by increased levels of PCNA expression (FIG. 10A), an indicator of cell proliferation (Harper et al., 1992). Levels of Bax/p21 protein was observed to be high in low-grade tumors, decreased in mid-grade tumors and further decreased in high-grade cancers (Table 1 and FIG. 10B). Furthermore, the low-grade prostate tumors containing high levels of Bax protein displayed low levels of Bax degradation activity while the high-grade tumors with reduced Bax expression had enhanced proteolytic activity for Bax (Table 1 and FIG. 10D). These data suggest a tight correlation among decreased Bax protein expression, increased Bax degradation activity and increased Gleason Scores in this subset of prostate cancer samples.

A correlation between Bax levels and Bax degradation activity, or tumor grade and Bax levels, or tumor grade and Bax degradation activity was searched for in all the samples. All 8 low-Bax-containing cases expressed high (5/8) or moderate (3/8) levels of Bax degradation activity, whereas most of 17 high-Bax-containing cases had low (9/17) or moderate (8/17) levels of Bax degradation activity (Fisher's exact test, p<0.05). Furthermore, all 6 high-grade tumors expressed low (4/6) or moderate (2/6) levels of Bax protein, whereas 17 out of 32 low- and mid-grade tumors contained high levels of Bax protein and only few of these cases (1/32) expressed low levels of Bax protein (p<0.05). Finally, all 6 cases of high-grade tumors contained high levels of Bax degradation activity, and most low-grade tumors contained low (8/32) or moderate (17/32) levels of Bax degradation activity (p<0.05). In contrast to Bax, no correlation was observed between levels of Bcl-2 protein and Gleason Scores of prostate cancer (Table 1). Furthermore, the levels of Bcl-2 degradation activity were only slightly increased in high-grade tumors (FIG. 10E).

To try to examine whether levels of Bax ubiquitination are also increased in advanced prostate cancers, Bax immunoprecipitates were prepared from different prostate tumor samples, followed by Western blotting using an ubiquitin antibody. Levels of a p55 were undetected in low-grade prostate tumor samples (Gleason Scores 3, 5), slightly increased in a grade-7 sample, and significantly increased in a grade-9 tumor specimen (FIG. 10F). The increased p55 levels were detected in several different high-grade prostate tumor samples. The data are consistent with increased levels of Bax ubiquitination and degradation during progression of prostate adenocarcinoma.

Discussion

In the present application, it is reported that: (i) proteasome inhibition results in Bax accumulation prior to release of cytochrome c and induction of apoptosis, which is associated with the ability of proteasome inhibitors to overcome Bcl-2-mediated antiapoptotic function; (ii) Bax is regulated by an ATP/ubiquitin/proteasome-dependent degradation pathway; (iii) decreased levels of Bax protein correlate with increased levels of Bax degradation in advanced human prostate cancer and further correlate with increased Gleason score in prostate cancer.

Previously, it was reported that proteasome inhibitors were able to induce apoptosis in human Jurkat cells over-expressing Bcl-2 protein (An et al., 1998). Another group also reported a similar finding using Bcl-2-overexpressing prostate cancer cells (Herrmann et al., 1998). In the current study, the molecular basis for the ability of proteasome inhibitors to overcome Bcl-2 antiapoptotic function was investigated. It was demonstrated that Bax, an inhibitor of Bcl-2, is a direct target of the proteasome (FIGS. 7–9). The following arguments shows that Bax accumulation by proteasome inhibition is associated with the proteasome inhibitor's ability to overcome the Bcl-2 protective function. First, Bax protein levels were increased prior to release of cytochrome c from mitochondria to the cytosol (FIG. 7E vs. FIG. 7A and FIG. 7C). Second, Bax was primarily accumulated in cytoplasm during proteasome inhibition; the observation that the increased Bax signals clustered around nuclei suggests accumulation in mitochondria (FIG. 8C). Third, proteasome inhibition-accumulated Bax protein was able to interact with Bcl-2 (FIG. 8D). Finally, Bcl-2 protein levels remained relatively unchanged during proteasome inhibition (FIG. 7F). The studies are consistent with the reported functional role of Bax and Bcl-2 proteins in forming ion-channels in mitochondria membrane where they regulate cytochrome c leakage into cytosol during apoptosis (Antonsson et al., 1997; reviewed in Green et al., 1998; Gross et al., 1999). It has been found that dephosphorylated Bad and cleaved Bid are able to interact with Bcl-XL or Bcl-2 in mitochondria and overcome their antiapoptotic function (Green et al., 1998; Gross et al., 1999). Whether proteasome inhibitors also induces dephosphorylation of Bad and cleavage of Bid in the systems remains to be investigated.

The cellular and cell-free studies have demonstrated that Bax is degraded via an ATP-/ubiquitin-dependent proteasome pathway (FIGS. 7–9). Treatment of cells with the proteasome inhibitor lactacystin (Fenteany et al., 1994) or LLnV (Rock et al., 1994) accumulated Bax protein (but not Bax mRNA) and the ubiquitinated forms of Bax (FIG. 7E. FIG. 8B, and FIG. 9A), whereas the cysteine protease inhibitor LLM (Rock et al., 1994) had no effect (FIG. 8B). In addition, Bax degradation activity was inhibited in cellular and cell-free assays by a proteasome inhibitor LLnV, LLL, LLnL or b-lactone, but not by the cysteine protease inhibitor LLM (FIG. 9B and FIG. 9C). Furthermore, cell-free Bax degradation was prevented by removal of the proteasome via ultracentrifugation or immunodepletion, which can be reconstituted by addition of the proteasome-enriched pellet fraction or a purified 20S proteasome (FIG. 9D and FIG. 9E). Finally, the cell-free Bax degradation process required ATP (FIG. 9F). All the above features of Bax degradation are similar to those of previously identified target proteins of ubiquitin/proteasome degradation pathway (Hochstrasser et al., 1995; Dou et al., 1999). Most recently, one group reported that Bax/p21 protein levels were increased when Hela or Saos-2 cells were treated with a proteasome inhibitor (Chang et al., 1998). However, applicants did not provide direct evidence for Bax as a target protein for the ubiquitin/proteasome pathway in their systems. Such direct evidence has been provided in the current studies.

Most recently, it has also been found that Bcl-2 is specifically degraded after stimulation of human endothelial cells with tumor necrosis factor-alpha (Dimmeler et al., 1999). Compared to cell-free Bax degration, no or much less Bcl-2 proteolysis was observed after incubation with a tumor cell or tissue extract (FIG. 9B, lower vs. upper; FIG. 10E vs. FIG. 10D). In addition, the tumor suppressor p53, another target of the ubiquitin/proteasome pathway (Hochstrasser et al., 1995; Dou et al., 1999), was much more resistant than Bax to induction of cell-free degradation (Li, B., Peng, Y., Chen, J. and Dou, Q.P., unpublished data). It seems that the in vitro degradation assay preferably detects degradation of Bax over Bcl-2 and p53.

Under cell-free conditions, in addition to proteasome-mediated degradation, Bax can also be cleaved by a calcium-dependent calpain activity (Wood et al., 1998). However, the following arguments suggest that the calpain-mediated Bax cleavage is not a major mechanism for regulation of Bax in the cell systems. First, the calpain cleavage product of Bax, Bax/p18 fragment, was not observed in exponentially growing Jurkat T cells (FIG. 7E, lane 1), suggesting that under in vivo conditions either Bax is not cleaved by the calpain or Bax/p18 is further cleaved or degraded. Second, treatment of Jurkat cells with the calpain inhibitor LLM, which blocked cell-free Bax cleavage to the p18 fragment (Wood et al., 1998), neither increased Bax/p21 levels nor induced apoptosis (FIG. 8A and FIG. 8B). Third, Bax/p18 was not detected during the process of proteasome inhibitor-induced apoptosis (FIG. 7E), although it was found in cells treated with an anticancer drug (Thomas et al., 1996). This difference is probably due to different apoptosis stimuli used. In any case, the results have demonstrated that inhibition of the proteasome, but not calpain, activity is responsible for the accumulation of Bax protein.

In the present application, it was also reported that decreased Bax levels correlated well with increased Bax degradation in aggressive prostate tumor samples, whereas no such a correlation was found between levels of Bcl-2 protein or Bcl-2 degradation activity and Gleason Scores of these tumor samples (Table 1 and FIG. 10). Furthermore, all high-grade tumors expressed low/moderate levels of Bax protein and high levels of Bax degradation activity, whereas most of low- and mid-grade tumors contained high levels of Bax protein and low/moderate levels of Bax degradation activity. It should be noted that two previous studies using immunohistochemical assay showed that Bax levels did not correlate with Gleason grade of prostate cancer (Krajewski et al., 1994; Mackey et al., 1998). This was probably due to that immunohistochemistry detected a mixture of Bax/p21 and ubiquitinated Bax while Western blotting was able to separate Bax/p21 from its modified forms.

The p55 band, found in both Jurkat T cells treated with a proteasome inhibitor (FIG. 9A) and high-grade prostate cancer tumor samples (FIG. 10F), can be recognized by antibodies to both Bax and ubiquitin proteins, suggesting that it is probably a poly-ubiquitinated form of Bax. This needs to be conformed by further investigation using cells expressing a tagged ubiquitin.

Human cancer biologic behavior must be controlled by complex molecular mechanisms. In addition, Bax is also regulated through multiple signal transduction pathways. The data suggest that Bax degradation is an important regulatory mechanism for controlling Bax protein levels, which plays an important role in advancing prostate cancer. Discovery of the correlation between proteasome-mediated Bax degradation and prostate cancer progression should have great clinical significance in diagnosis, treatment and prognosis of human prostate and other cancers.

Example 2

A proteasome inhibitior at low concentrations induces programmed cell death (apoptosis) preferentially in multiple human cancer and transformed cell lines, including those overexpressing Bcl-2 or Bcr-Abl oncoprotein. The proteasome inhibition-induced cancer cell apoptosis is tightly associated with accumulation of the pro-apoptotic Bax protein to mitochondria, and consequent release of cytochrome c into cytosol. In contrast, the same proteasome inhibitor treatment of human normal cells fails to accumulate Bax, and consequently fails to induce cytochrome c-dependent activation of apoptotic pathway, although the proteasome inhibitors at much higher concentrations were able to induce Bax- and cytochrome c-independent apoptotic death in human normal fibroblasts.

Putative roles of retinoblastoma protein in apoptosis (Dou et al., 1995). Most recent studies suggest that the tumor suppressor RB protein plays a regulatory role in apoptosis. During the onset of apoptosis, the hyperphosphorylated form of RB (p120/hyper) is converted to a hypophosphorylated form (p115/hypo), which is mediated by a specific protein-serine/threonine phosphatase activity (Dou et al., 1995). Accompanied by the internucleosomal fragmentation of DNA, the newly formed p115/hypo/RB is immediately cleaved by a caspase activity (An et al., 1996; Fattman et a., 1997). By contrast, the unphosphorylated form of RB (p110/unphos) remains uncleaved during apoptosis (Dou et al., 1995). Further studies suggest that p110/unphos/RB functions as an inhibitor of apoptosis. Therefore, a balance between RB phosphatases and kinases and consequent RB phosphorylation status can be important for the determination of cellular fate.

Proteasome inhibitors overcome Bcl-2 protective function and selectively induce apoptosis in transformed, but not normal, human fibroblasts (An et al., in press). It is reported that a novel dipeptidyl proteasome inhibitor, CEP1612, at low concentrations rapidly induces apoptosis in human Jurkat T cells overexpressing Bcl-2 and also in all human prostate, breast, tongue and brain tumor cell lines were tested to date, without exception. Other proteasome inhibitors, including tripeptidyl aldehyde and lactacystin, have similar effects. In contrast, etoposide, a standard anticancer drug, fails to kill these cells when employed under the same conditions. The apoptosis-inducing abilities of CEP1612 and its analogous compounds match precisely their order for inhibition of the proteasome chymotrypsin-like activity. CEP1612-induced apoptosis is p53-independent, inhibitable by a tetrapeptide caspase inhibitor, and associated with accumulation of the cyclin-dependent kinase inhibitors p21 and p27. Furthermore, CEP1612 selectively accumulates p27 and induces apoptosis in simian virus 40-transformed, but not the parental normal, human fibroblasts.

Proteasome inhibition leads to significant reduction of Bcr-Abl expression and subsequent induction of apoptosis in K562 human chronic myelogenous leukemia cells (Dou et al., 1999). Proteasome plays a role in regulating Bcr-Abl function. It is demonstrated by using a variety of inhibitors that inhibition of the proteasome, but not cysteine protease, activity is able to activate the apoptotic cell death program in K562 cells, which can be blocked by a specific caspase-3-like tetrapeptide inhibitor. Western blot analysis using specific antibodies to c-Abl and Bcr proteins show that treatment of K562 cells with a proteasome inhibitor results in significant reduction of Bcr-Abl protein expression, which occurs several hours before the onset of apoptotic execution. Levels of c-Abl/p145 and Bcr/p160 proteins, however, remain essentially unaltered at that time. Furthermore, reduced Bcr-Abl expression is reflected in significantly attenuated Bcr-Abl-mediated protein tyrosine phosphorylation.

Proteasome inhibitors overcome Bcl-2- and Bcr-Abl-mediated protection through accumulating Bax and subsequently inducing cytochrome c-dependent apoptosis (Li et al, 1999). The molecular mechanisms responsible for how proteasome inhibition induces apoptosis in cells overexpressing Bcl-2 or Bcr-Abl oncoprotein have been investigated. It was found that inhibition of the proteasome activity in Bcl-2- and Bcr-Abl-overexpressing cell lines accumulates the pro-apoptotic Bax protein to mitochondria, and consequently induces release of cytochrome c into cytosol and activation of caspase-mediated apoptotic pathway. Consistent with the hypothesis that Bax is a direct target of the proteasome, treatment with a proteasome inhibitor increased levels of several polypeptides that contain ubiquitinated Bax, but such a treatment did not increase the levels of Bax mRNA. The data demonstrate that inhibition of the ubiquitin/proteasome-mediated Bax degradation is sufficient to overcome Bcl-2- and Bcr-Abl-mediated protective function from apoptosis.

Figure 1A:
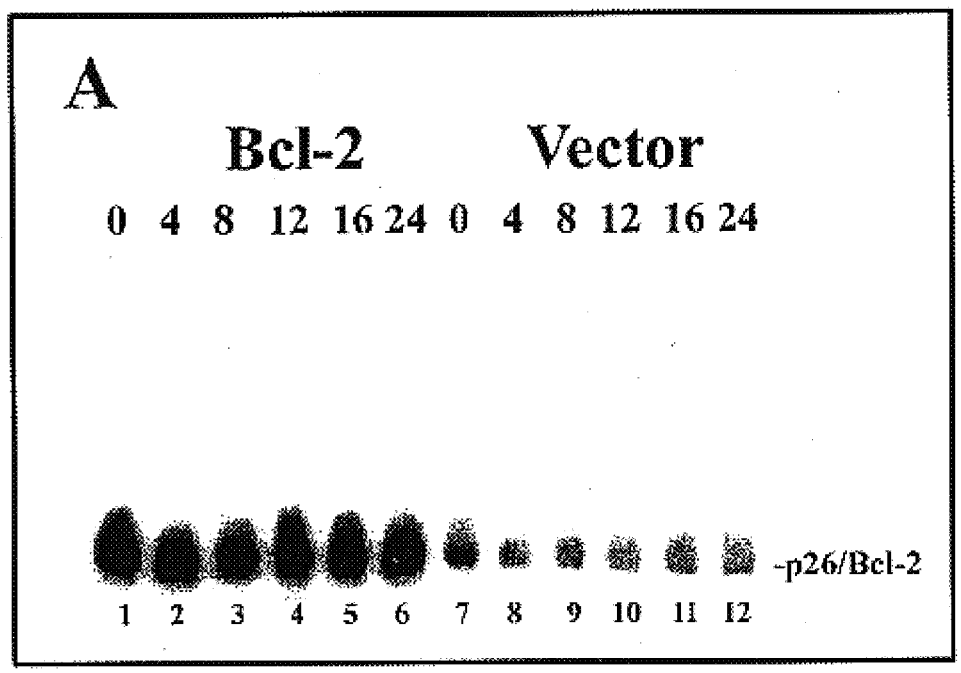
FIGS. 1A and 1B show that Bcl protein does not undergo any post-translation or modification during proteasome inhibition.

FIG. 1A shows that Bcl-2 protein does not undergo any post-translational modification during proteasome inhibition. Jurkat T cells overexpressing Bcl-2 (lanes 1–6) or vector (lanes 7–12) were treated with 50 microM LLnV for up to 24 hours, followed by Western blot assay using an anti-Bcl-2 antibody.

Figure 1B:
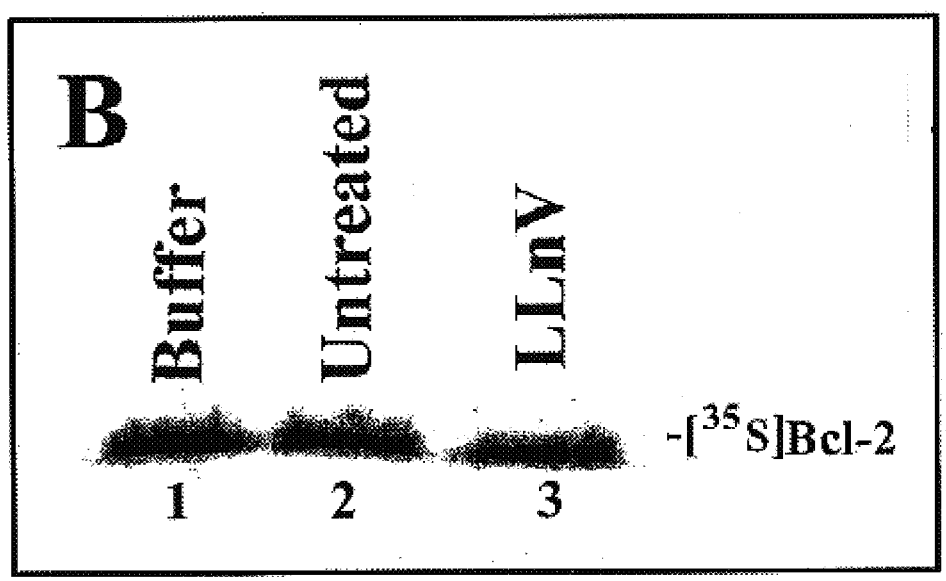

FIG. 1B shows that no Bcl-2 degradation activity was detected in growing cancer cells. Exponentially grown Jurkat T cells (untreated) were treated with 50 mM LLnV for 8 hours, followed by preparation of whole cell extracts. The prepared extracts (100 microg protein/reaction), or a sample buffer, were incubated with 0.7 microl of [$^{35}$S]-labeled, in vitro-translated Bcl-2 protein at 37° C. for 4 hours, followed by electrophoresis and autoradiography.

Human cancer cells selectively degrade the proapoptotic Bax protein, but not the antiapoptotic Bcl-2 protein. In contrast to Bax (Li et al., 1999), proteasome inhibition did not induce any apparent post-translational modifications on Bcl-2, including phosphorylation, ubiquitination and proteolytic cleavage (Figure X, panel A). To confirm that, a cell-free degradation assay was developed using a [$^{35}$S]-labeled, in vitro-translated Bax or Bcl-2 as a substrate. When incubated with a whole cell extract of growing Jurkat T cells, the level of labeled Bax was dramatically decreased (similar to FIG. 4A, lower panel, lanes 2, 4 vs. 1). This decrease is not due to $Ca^{2+}$-dependent, calpain-mediated Bax cleavage (see Wood et al., 1998) since not only $Ca^{2+}$ was not added but also a calpain inhibitor LLM was used in the cell-free system. In contrast to Bax, the level of the labeled Bcl-2 was unchanged after in vitro incubation (Figure X, panel B, lanes 2 vs. 1). When cells were pretreated with the proteasome inhibitor LLnV, the Bax degradation activity in the cell extract was inhibited (similar to FIG. 4A, lower panel, lanes 3 vs. 2 and lanes 5 vs. 4). However, LLnV pretreatment had no effects on levels of labeled Bcl-2 after in vitro incubation (Figure X, panel B, lanes 3 vs. 2). The data suggests that selective degradation of the proapoptotic Bax, but not the antiapoptotic Bcl-2, protein is a novel survival mechanism used by human cancer cells.

Proteasome inhibitors activate Bax- and cytochrome c-dependent apoptosis pathway preferentially in transformed human fibroblasts. Normal human fibroblasts are more resistant to proteasome inhibitor-induced apoptosis than transformed and cancer cells (An et al., in press). This is probably due to inability of the normal cells to accumulate Bax protein in response to proteasome inhibition, and consequently failure to release cytochrome c. To test this hypothesis, both SV40-transformed and normal WI-38 cells were treated with 50 microM LLnV for up to 24 hours, followed by measurement of PARP cleavage, cytochrome c release and Bax accumulation. Both cleavage of PARP and release of cytochrome c were detected in the transformed cells at 8 hours after LLnV treatment (FIGS. 1A, 1B, lanes 1–7). In contrast, only after 24 hours treatment, low levels of p85/PARP fragment and cytosolic cytochrome c were detected in normal WI-38 cells (FIGS. 1, A, B, lanes 8–14). Bax levels were dramatically increased prior to release of cytochrome c in the transformed cells after treatment with LLnV, but not DMSO (FIG. 1C). The levels of Bax/p21 were increased at as early as 4 hours and remained high afterwards. The level of a band of ~70 kDa was dramatically increased after 6 hours and remained very high afterwards. The level of another band of ~47 kDa increased at 4 hours, further increased between 6 and 12 hours, and then decreased (FIG. 1C). The p70 and p47 bands can contain ubiquitinated forms of Bax since similar polypeptides were detected by antibodies to both Bax and ubiquitin (Li et al., 1999). Furthermore, proteasome inhibition also increased the half-life of Bax protein in the transformed human fibroblasts, as demonstrated by the increased level of immunoprecipitated, $^{35}$S-labeled Bax protein (FIG. 1D, lanes 2 vs. 1). In another experiment, after 14 hours treatment with LLnL at up to 200 microM, normal WI-38 cells neither release cytochrome c nor accumulate Bax (FIGS. 2B, 2C), although they underwent apoptosis as judged by PARP cleavage (FIG. 2A). Therefore, although unable to activate the Bax- and cytochrome c-dependent apoptotic pathway in response to a low concentration of a proteasome inhibitor, normal cells are capable of undergoing Bax- and cytochrome c-independent apoptosis in response to a proteasome inhibitor at higher concentrations. In contrast to Bax, levels of the cdk inhibitor p21 in the normal cells were significantly increased by the LLnL treatment (FIG. 2D), supporting the idea that p21 is a proteasome target (Blagosklonny et al. 1996). The data demonstrate that regulation of Bax in normal human fibroblasts is different from that of p21, which is LLnL inhibitable.

FIG. 2 shows that proteasome inhibitor LLnV activates Bax- and cytochrome c-dependent apoptosis pathway preferentially in SV-40 transformed human fibroblasts. SV40-transformed (VA-13) and normal WI-38 cells were treated with 50 microM LLnV or DMSO (letter D) for up to 24 hours, followed by measurement of PARP cleavage (A), cytochrome c release (B) and Bax accumulation (C; also see FIG. 2). Panel D, exponentially grown VA-13 cells were pretreated with 50 microM LLnV or DMSO for 1 hour, washed with methionine-free medium, and then incubated for 30 minutes in methionine-free medium plus 50 microM LLnV (or DMSO). This was followed by replacing fresh methionine-free medium containing 150 microCi/ml of [$^{35}$S]-methionine, 10% dialyzed FBS and 50 microM LLnV (or DMSO). Cells were further incubated for 6 hours, followed by preparation of [$^{35}$S]-labeled protein lysates and Bax immunoprecipitates (6A7, PharMingen). The labeled Bax bands are indicated. FIG. 2E shows that whole cell extracts were prepared from exponentially grown VA-13, WI-38 or MCF-7 cells, followed by Western blotting (with anti-Bax antibody) or in vitro Bax degradation assay (Li et al., 1999). Bax-alpha subcloned into pcDNA3 was used for coupled in vitro transcription/translation in the presence of [$^{35}$S]methionine. For Bax cleavage assay, the whole cell extracts were prepared. The [$^{35}$S]-labeled Bax (0.7 microl) was incubated with 50 microg protein in assay buffer (containing 50 microM LLM and no Ca$^{2+}$) for 4 hours at 37° C. Following incubation, the samples were subjected to SDS gel electrophoresis and autoradiography.

Toward the goal of understanding why inhibition of the proteasome activity in normal human fibroblasts fails to accumulate Bax protein (FIG. 2, D vs. C), basal levels of Bax and Bax degradation activity were compared in both normal and transformed WI-38 cells. It was found that the Bax level was slightly lower in the normal than the transformed cells (FIG. 1E, top panel, lanes 2 vs. 1). This is probably due to a slightly higher level of Bax degradation activity in normal than in the transformed cells (FIG. 1E, lower panel, lanes 2 vs. 1). The slightly higher BDA activity in the normal cells should not be responsible for failure of these cells to accumulate Bax because these cells are still unable to accumulate Bax even after exposed to a proteasome inhibitor at much higher concentrations (FIG. 2C). Therefore, although the Bax degradation pathway is intact in normal human WI-38 cells, addition of a proteasome inhibitor somehow cannot block degradation of Bax and consequently, cannot trigger cytochrome c-dependent apoptosis.

Proteasome inhibitors selectively induce apoptosis in human breast cancer, but not normal, cells. Treatment with the specific proteasome inhibitor lactacystin (FIG. 3) or LLnV selectively induced cellular detachment of human breast cancer (SK-BR-3, MDA-MB-468), but not normal (MCF-10A), cells. Cells of both human breast cancer lines became detached in a lactacystin-concentration-dependent manner (FIG. 3). No detachment was induced in the normal human breast cells MCF-10A after treatment with lactacystin for 48 hours (FIG. 3) or even 72 hours. Proteasome inhibition-induced detachment of breast cancer cells is due to apoptosis (An et al., in press).

Levels of BDA predict levels of Bax and consequently influence sensitivity of human cancer cells to proteasome inhibitor-induced apoptosis. Basal level of Bax protein in SV40-transformed WI-38 cells (VA13) was several-fold higher than that of human breast cancer MCF-7 cells (FIG. 1E, top panel, lanes 1 vs. 3). This is due to a much lower level of BDA in VA13 cells than in MCF-7 cells (FIG. 1E, lower panel, lanes 1 vs. 3). This conclusion is further confirmed by using increased amounts of protein extracts of each cell line in the cell-free BDA assay (FIG. 4A, top panel). The BDA activity is inhibited when cells of each line were pretreated with the proteasome inhibitor LLnV; a greater inhibition was observed in VA-13 than in MCF-7 cells (FIG. 4A, lower panel), consistent with the observation that the BDA level in VA-13 cells was lower. In addition, in response to LLnV treatment, VA-13 cells rapidly accumulated Bax protein and subsequently induced apoptosis, as measured by PARP cleavage (FIG. 4B, lanes 1–5). In contrast, when MCF-7 cells were treated under the same conditions, Bax levels were not increased; PARP was cleaved only after 24 hours treatment, which is Bax-independent (FIG. 4B, lanes 6–9). Therefore, although highly preliminary, it appears that levels of BDA determine levels of Bax and consequently affect responsiveness of human cancer cells to proteasome inhibition-induced apoptosis.

Bax phosphorylation in vitro. Recent evidence indicates that phosphorylation triggers ubiquitin/proteasome-dependent degradation of several proteins (Ciechanover et al., 1998), including the transcription factor NF-kB (Verma et al., 1995), inhibitor of NF-kB (IkB; Verma et al., 1995), cyclin D1 (Diehl et al., 1997), cyclin E (Won et al., 1996), and the cdk inhibitor p27 (Vlach et al., 1997). Bax phosphorylation triggers its ubiquitin/proteasome-dependent degradation. If so, growing cancer cells that contain high levels of Bax degradation activity (Li et al., 1999 and FIGS. 1, 4) should also contain a Bax kinase activity. Indeed, an unlabeled Bax protein, prepared via in vitro transcription/translation using unlabeled amino acids, was phosphorylated after incubation at 37° C. for 1 hour with [gamma-$^{32}$P]ATP and a protein extract of exponentially grown HL-60 or Jurkat T cells (FIG. 5B, lanes 1, 2). The phosphorylated protein migrated to a position of ~21 kDa, supporting the idea that it is phosphorylated Bax. Apoptotic cells containing a higher level of Bax and a lower level of Bax degradation activity should also contain a low level of the Bax kinase activity. To test that, a protein extract was prepared from apoptotic Jurkat T cells (FIG. 5A, right vs. left panels), and incubated with the unlabeled Bax in the presence of [gamma-$^{32}$P]ATP. No Bax phosphorylation was observed from this experiment (FIG. 5B, lanes 3 vs. 2). Therefore, it is possible that growing cancer cells contain high levels of both Bax kinase activity and Bax degradation activity, both of which should be decreased when cancer cells undergo apoptosis. The data support the hypothesis that Bax phosphorylation is important for its proteolytic degradation.

Figure 6A:
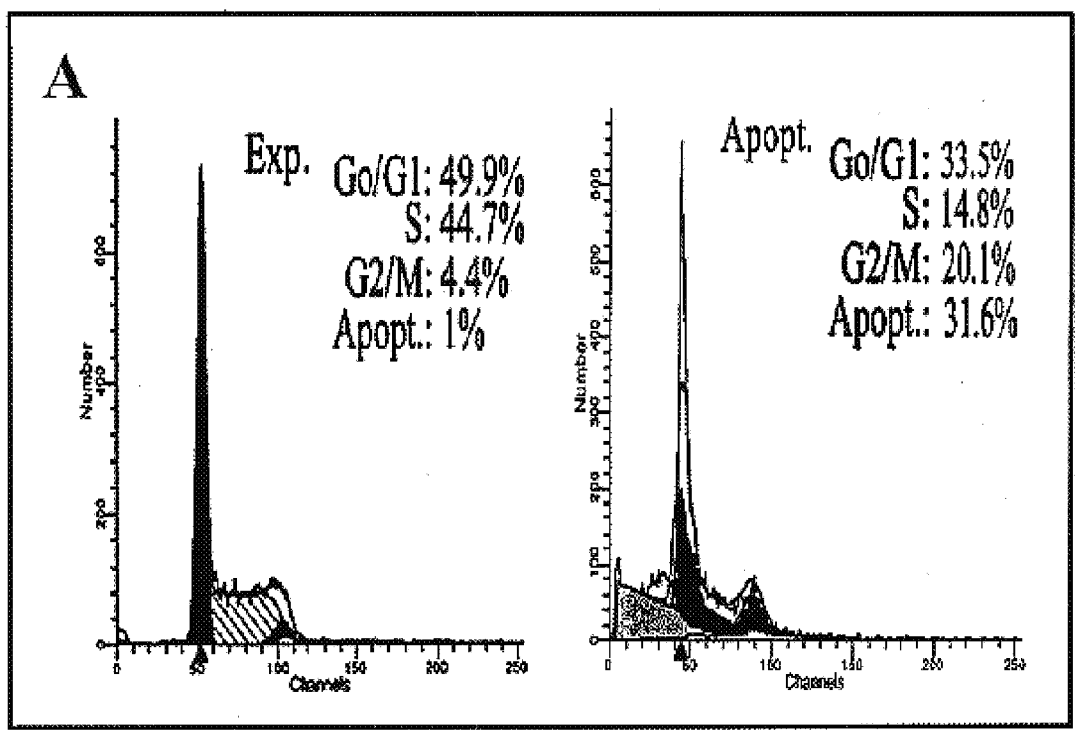
FIGS. 6A and 6B show photographs showing the flow cytometry where exponentially grown human Jurkat T cells were induced to undergo apoptosis by withdrawing serum for 48 hours.
Figure 6B:
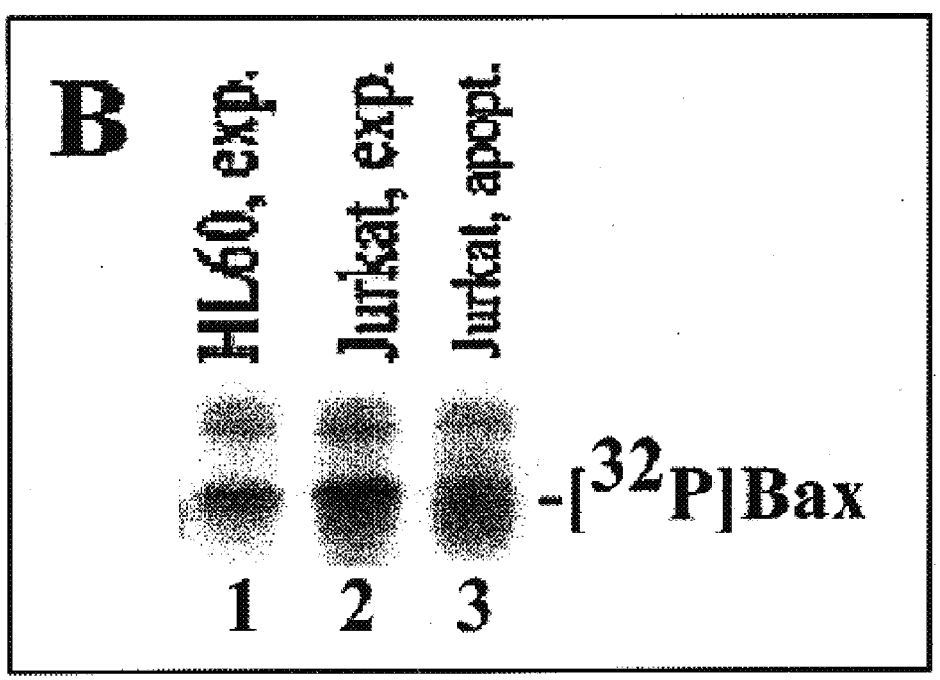

FIG. 6A shows the flow cytometry. Exponetially grown human Jurkat T cells (Exp) were induced to undergo apoptosis by withdrawing serum for 48 hours (Apopt.), followed by flow cytometry analysis. Apoptotic population was increased by 30% as indicated. FIG. 6B shows in vitro Bax phosphorylation assay. Aliquots of cells from A were used to make whole cell extracts (Dignam et al., 1993) (lanes 2, 3). The prepared extracts (50 microg protein/reaction) were incubated with 2 microl of an unlabeled, in vitro-translated Bax protein and 10 microCi [gamma-$^{32}$P]ATP at 37° C. for 1 hour, followed by electrophoresis and autoradiography (Dou et al., 1993). The phosphorylated Bax is indicated. Lane 1 was from a protein extrat of exponentially grown HL-60 cells.

Example 3

Previously it was reported that proteasome inhibitors have the ability to induce tumor cell death (apoptosis). This example screens for potent proteasome inhibitors in vitro and in vivo from any compound drug library, more specifically in this example, the NCI Diversity Set was screened.

A proteasome activity assay was developed using a 96-well plate. Briefly, whole cell extracts were prepared from growing human Jurkat T cells, which contain high levels of the chymotrypsin-like activity of the proteasome. In each well of a 96-well plate, 10 microg protein extract was mixed with 20 microM fluorogenic proteasome peptide substrate and 5 microM of a putative proteasome inhibitor, in this example, the NCI Diversity Set drug to be examined or 5 microM of the authentic peptide proteasome inhibitor LLL (as a control) in 100 microliter of assay buffer. The mixture was incubated for 1 hour at 37° C., followed by direct measurement of released products (AMCs groups) using a Wallac Victor 2 plate-reader using Umbelliferone setting (355 nm/460 nm).

By performing this assay, all the ~2,000 compounds of the NCI Diversity Set were screened, and 14 compounds were obtained that exhibited potent proteasome inhibitory activity (80–93% inhibition at 5 microM) equivalent to the potency of LLL.

Next, the ability of these 14 compounds to inhibit the proteasome in tumor cells and the ability of these compounds to induce tumor growth arrest or cell death/apoptosis was measured.

HL-60, Jurkat T, K562 (overexpressing Bcl-Abl oncogene) and Jurkat T cells overexpressing Bcl-2 protein are used for these in vivo studies.

To measure inhibition of the proteasome activity in vivo, tumor cells, cultured in 24-well plates, are first incubated for 12 hours with various concentrations of the selected putative proteasome inhibitors or LLL (as a control), followed by an additional 2 hour-incubation with a fluorogenic peptide substrate. After that, cell medium (200 microliter) is collected and used for measurement of free AMCs. The accumulation of natural proteasome target proteins (i.e., p27, p21 and Bax) and their ubiquitinated forms is also measured.

Growth arrest of tumor cells is measured by flow cytometry. Apoptotic cell death is measured by TUNEL, cytochrome c release, PARP cleavage and trypan blue incorporation.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

TABLE 1

Correlation between Bax/p21 protein levels or degradation activities and tumor grade in human prostate adenocarcinomas

| Tumor #. | Tumor Grade (Gleason Score) | Bax Protein Level | Bax Degradation Activity | Bcl-2 Protein Level |
|---|---|---|---|---|
| 1 | 3 | +++ | + | +++ |
| 2 | 5 | +++ | + | N/A |
| 3 | 5 | +++ | + | +++ |
| 4 | 6 | +++ | + | N/A |
| 5 | 6 | +++ | + | ++ |
| 6 | 6 | +++ | + | + |
| 7 | 6 | +++ | ++ | ++ |
| 8 | 7 | +++ | ++ | ++ |
| 9 | 7 | ++ | ++ | +++ |
| 10 | 7 | + | ++ | +++ |
| 11 | 7 | + | ++ | + |
| 12 | 7 | + | +++ | + |
| 13 | 8 | + | +++ | + |
| 14 | 9 | + | +++ | + |

TABLE 1-continued

Correlation between Bax/p21 protein levels or degradation activities and tumor grade in human prostate adenocarcinomas

| Tumor #. | Tumor Grade (Gleason Score) | Bax Protein Level | Bax Degradation Activity | Bcl-2 Protein Level |
|---|---|---|---|---|
| 15 | 9 | + | +++ | ++ |
| 16 | 10 | + | +++ | ++ |

Protein levels were assessed by immoblot:
+++, detected of a very strong signal (high);
++, detected of a strong signal (moderate);
+, detected of a weak signal (low),
N/A, not available.
The intensity of the immunoblotting signals for Bax/p21 or Bcl-2 levels was normalized by comparison to actin levels in each sample. Bax degradation activity was assessed by comparison to buffer only control after 4 h incubation:
+, <30% degradation (low);
++, 30–60% degradation moderate); >60% degradation (high).

REFERENCES

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" *Science* 244:1288–1292 (1989).

Davies et al., "Targeted alterations in yeast artificial chromosomes for inter-species gene transfer", *Nucleic Acids Research*, Vol. 20, No. 11, pp. 2693–2698 (1992).

Dickinson et al., "High frequency gene targeting using insertional vectors", *Human Molecular Genetics*, Vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Huxley et al., "The human HPRT gene on a yeast artificial chromosome is functional when transferred to mouse cells by cell fusion", *Genomics*, 9:742–750 (1991).

Jakobovits et al., "Germ-line transmission and expression of a human-derived yeast artificial chromosome", *Nature*, Vol. 362, pp. 255–261 (1993).

Lamb et al., "Introduction and expression of the 400 kilobase precursor amyloid protein gene in transgenic mice", *Nature Genetics*, Vol. 5, pp. 22–29 (1993).

Pearson and Choi, *Expression of the human b-amyloid precursor protein gene from a yeast artificial chromosome in transgenic mice*. Proc. Natl. Acad. Sci. USA, 1993. 90:10578–82.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Schedl et al., "A yeast artificial chromosome covering the tyrosinase gene confers copy number-dependent expression in transgenic mice", *Nature*, Vol. 362, pp. 258–261 (1993).

Strauss et al., "Germ line transmission of a yeast artificial chromosome spanning the murine $a_1$ (I) collagen locus", *Science*, Vol. 259, pp. 1904–1907 (1993).

Gilboa, E, Eglitis, M A, Kantoff, P W, Anderson, W F: Transfer and expression of cloned genes using retroviral vectors. BioTechniques 4(6):504–512, 1986.

Cregg J M, Vedvick T S, Raschke W C: Recent Advances in the Expression of Foreign Genes in *Pichia pastoris*, Bio/Technology 11:905–910, 1993.

Culver, 1998. Site-Directed recombination for repair of mutations in the human ADA gene. (Abstract) Antisense DNA & RNA based therapeutics, February, 1998, Coronado, Calif.

Huston et al., 1991 "Protein engineering of single-chain Fv analogs and fusion proteins" in Methods in Enzymology (J J Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88–99.

Mernaugh and Mernaugh, 1995 "An overview of phage-displayed recombinant antibodies" in Molecular Methods In Plant Pathology (R P Singh and U S Singh, eds.; CRC Press Inc., Boca Raton, Fla.) pp. 359–365.

Steller, H. (1995) *Science* 267, 1445–1462.

Green, D. R., & Reed, J. C. (1998) *Science* 281, 1309–1312.

Gross, A., McDonnel, J. M. & Korsmeyer, S. J. (1999) *Genes Dev.* 13, 1899–1911.

Martin, S. J. & Green, D. R. (1995) *Cell* 82, 349–352.

Thornberry, N. A. & Lazebnik, Y. (1998) *Science* 281, 1312–1316.

Lazebnik, Y. A., Kaufmann, S. H., Desnoyers, S., Poirier, G. G., & Earnshaw, W. C. (1994) *Nature* 371, 346–347.

An, B., & Dou, Q. P. (1996) *Cancer Res.* 56, 438–442.

Hochstrasser, M. (1995) *Curr Opin. Cell Biol.* 7, 215–223.

Dou, Q. P., & Li, B. (1999) *Drug Resist. Updates* 2, 215–223.

Imajoh-Ohmi, S., Kawaguchi, T., Sugiyama, S., Tanaka, K., Omura, S., & Kikuchi, H. (1995) *Biochem. Biophys. Res. Commun.* 217,1070–1077.

Drexler, H. C. (1997) *Proc. Natl. Acad. Sci. USA* 94, 855–860.

Lopes, U. G., Erhardt, P., Yao, R., & Cooper, G. M. (1997) *J. Biol. Chem.* 272, 12893–12896.

An, B., Goldfarb, R. H., Siman, R., & Dou, Q. P. (1998) *Cell Death Differ.* 5, 1062–4075.

Dou, Q. P., McGuire, T. F., Peng, Y. B., & An, B. (1999) *J Pharmacol. Exp. Ther.* 289, 781–790.

Loda, M., Cukor, B., Tam, S. W., Lavin, P., Fiorentino, M., Draetta, G. F., Jessup, J. M., & Pagano, M. (1997) *Nat. Med.* 3, 231–234.

Fang, G., Chang, B. S., Kim, C. N., Perkins, C., Thompson, C. B., & Bhalla, K. N. (1998) *Cancer Res.* 58, 3202–3208.

Wood, D., Thomas, A., Devi, L. A., Berman, Y., Beavis, R. C., Reed, J. C., & Newcomb, E. W. (1998) *Oncogene* 17, 1069–1078.

Bossy-Wetzel, E., Newmeryer, D. D., & Green, D. R. (1998) *EMBO J.* 17, 37–49.

Wang, T. T. Y., & Phang, J. M. (1995) *Cancer Res.* 55, 2487–2489.

Barrell, B. G., Bankier, A. T., & Drouin, J. (1979) *Nature* 282, 189–194.

Rock, K. L., Gramm, C., Rothstein, L., Clark, K., Stein, R., Dick, L., Hwang, D., & Goldberg, A. L. (1994) *Cell* 78, 761–771.

Fenteany, G., Standaert, R. F., Lane, W. S., Choi, S., Corey, E. J., & Schreiber, S. L. (1995) *Science* 268, 726–731.

Fenteany, G., Standaert, R. F., Reichard, G. A., Corey, E. J., & Schreiber, S. L. (1994) *Proc. Natl. Acad. Sci. USA* 91, 3358–3362.

Harper, M. E., Glynne-Jones, E., Goddard, L., Wilson, D. W., Matenhelia, S. S., Conn, I. G., Peeling, W. B., & Griffiths, K. (1992) *Prostate* 20, 243–253.

Herrmann, J. L., Briones, F. Jr, Brisbay, S., Logothetis, C. J., & McDonnell, T. J. (1998) *Oncogene* 17, 2889–2899.

Antonsson, B., Conti, F., Ciavatta, A., Montessuit, S., Lewis, S., Martinou, I., Bernasconi, L., Bernard, A., Mermod, J. J., Mazzei, G., Maundrell, K., Gambale, F., Sadoul, R., & Martinou, J. C. (1997) *Science* 277, 370–372.

Chang, Y. C., Lee, Y. S., Tejima, T., Tanaka, K., Omura, S., Heintz, N. H., Mitsui, Y., & Magae, J. (1998) *Cell Growth Differ.* 9, 79–84.

Dimmeler, S., Breitschopf, K., Haendeler, J., & Zeiher, A. M. (1999) *J. Exp. Med.* 189, 1815–1822.

Thomas, A., E I Rouby, S., Reed, J. C., Krajewski, S., Silber, R., Potmesil, M., & Newcomb, E. W. (1996) *Oncogene* 12, 1055–1062.

Krajewski, S., Krajewska, M., Shabaik, A., Miyashita, T., Wang, H. G., & Reed, J. C. (1994) *Am. J. Pathol.* 145, 1323–1336.

Mackey, T. J., Borkowski, A., Amin, P., Jacobs, S. C., & Kyprianou, N. (1998) *Urology* 52, 1085–1090.

Lee S, Christakos S, Small M B. Apoptosis and signal transduction: clues to a molecular mechanism. Curr. Opin. Cell Biol. 1993; 5: 286–291.

Dou Q P, An B, Will P L. Induction of a retinoblastoma phosphatase activity by anticancer drugs accompanies p53-independent G1 arrest and apoptosis. Proc. Natl. Acad. Sci. USA 1995; 92: 9019–9023.

Linette, G. P., Li Y, Roth, K., Korsmeyer, S. J. Cross talk between cell death and cell cycle progression: Bcl-2 regulates NFAT-mediated activation. Proc. Natl. Acad. Sci. USA 1996; 93: 9545–9552

Dou Q P. Putative roles of retinoblastoma protein in apoptosis. Apoptosis. 1997; 2: 5–8.

Wylie, A. H., Kerr, J. F. R., Currie, A. R. Cell Death: The Significance of Apoptosis. Int. Rev. Cytol. 1980; 68: 251–306

Earnshaw, W. C. Nuclear Changes in Apoptosis. Curr. Opin. Cell Biol. 1995; 7: 337–343

Steller, H. Mechanisms and genes of cellular suicide. Science 1995; 267: 1445–1449.

Hartwell, L. H, Kastan, M. B. Cell cycle control and cancer. Science 1994; 266: 1821–1828.

Evan, G. and Littlewood, T. A Matter of Life and Cell Death. Science 1998; 281:1317–1322

Reed J. C. Bcl-2 and the Regulation of Programmed Cell Death. J. Cell Biol. 1994; 124: 1–6.

Green, D. R. and Reed, J. C. Mitochondria and Apoptosis. Science 1998; 281: 1309–1312.

Cory, S. and Adams, J. M. The Bcl-2 Protein Family: Arbiters of Cell Survival. Science 1998; 281: 1322–1326.

Wang, H-. G. and Reed, J. C. Mechanisms of Bcl-2 Protein Function. Histol Histopathol 1998; 13: 521–530.

Thornberry, N. A. and Lazebnik, Y. Caspases: Enemies Within. Science 1998, 281: 1312–1316

Tsujimoto, Y., Cossman, J., Jaffe, E., Croce, C. Involvement of the bcl-2 proto-oncogene expression of cellular sensitivity to tumor necrosis factor-mediated cytotoxicity. Oncogene 1985; 8: 1440–1443.

Martin S J, Green D R. Protease activation during apoptosis: death by a thousand cuts? Cell 1995; 82: 349–352.

Lazebnik, Y. A, Kaufmann, S. H., Desnoyers, S., Poirier, G. G, Earnshaw, W. C. Cleavage of poly(ADP-ribose) polymerase by a proteinase with properties like ICE. Nature 1994; 371: 346–347.

Kayalar, C., Ord, T., Testa, M. P, Zhong, L.-T, Bredesen, D. E. Cleavage of actin by interleukin-1b-converting enzyme to reverse DNase I inhibition. Proc. Natl. Acad. Sci. USA 1996; 93: 2234–2238.

Wang, X., Zelenski, N. G., Yang, J., Sakai, J., Brown, M. S., Goldstein, J. L. Cleavage of sterol regulatory element binding proteins (SREBPs) by CPP32 during apoptosis. EMBO J. 1996; 15: 1012–1020.

Song, Q., Lees-Miller, S. P., Kumar, S., Zhang, N., Chan, D. W., Smith, G. C. M., Jackson, S. P, Alnemri, E. S., Litwack, G., Khanna, K. K., Lavin MF. DNA-dependent protein kinase catalytic subunit: a target for an ICE-like protease in apoptosis. EMBO J. 1996; 15: 3238–3246.

An, B., Dou, Q. P. Cleavage of retinoblastoma protein during apoptosis: an interleukin 1b-converting enzyme-like protease as candidate. Cancer Res. 1996; 56: 438–442.

Fattman, C. L., An, B., Dou, Q. P. Characterization of interior cleavage of retinoblastoma protein in apoptosis. J. Cell. Biochem. 1997; 67: 399–408.

Dou, Q. P, An, B., Antoku, K., Johnson, D. E. Fas stimulation induces RB dephosphorylation and proteolysis that is blocked by inhibitors of the ICE-like protease family. J. Cell. Biochem. 1997; 64: 586–594.

Janicke, R. U., Walker, P. A., Lin, X. Y., Porter A G. Specific cleavage of the retinoblastoma protein by an ICE-like protease in apoptosis. EMBO J. 1996; 15: 6969–6978.

Tan X, Martin S J, Green D R, Wang Y J. Degradation of retinoblastoma protein in tumor necrosis factor and CD95-induced cell death. J. Biol. Chem. 1997; 272: 9613–9616.

Hochstrasser, M. Ubiquitin, proteasomes, and regulation of intracellular protein degradation. Curr. Opin. Cell Biol. 1995; 7: 215–223.

Ciechanover, A. The ubiquitin-proteasome proteolytic pathway. Cell 1994; 79: 13–21.

Rock K L, Gramm C, Rothstein L, Clark K, Stein R, Dick L, Hwang D and Goldberg A L. Inhibition of the proteasome block the degradation of most cell proteins and generation of peptides presented on MHC class I molecules. Cell 1994; 78: 761–771.

Fenteany, G., Standaert, R. F, Lane, W. S, Choi S, Corey, E. J, Schreiber, S. L. Inhibition of proteasome activities and subunit-specific amino-terminal threonine modification by lactacystin. Science 1995; 268: 726–731.

Imajoh-Ohmi, S., Kawaguchi, T., Sugiyama, S., Tanaka, K., Omura, S., Kikuchi, H. Lactacystin, a specific inhibitor of the proteasome induces apoptosis in human monoblast U937 cells. Biochem. Biophy. Res. Commu. 1995; 217: 1070–1077.

Shinohara, K., Tomoku, M., Nakano, H., Tone, S., Ito, H., Kawashima, S. Apoptosis induction resulting from proteasome inhibition. Biochem. J. 1996; 317: 385–388.

Drexler, H. C. A. Activation of the cell death program by inhibition of proteasome function. Pro. Natl. Acad. Sci. USA. 1997; 94: 855–860.

Lopes, U. G., Erhardt, P., Yao, R., Cooper, G. M. p53-dependent induction of apoptosis by proteasome inhibitors. J. Biol. Chem. 1997; 272: 12893–1896.

An, B., Goldfarb, R. H., Siman, R., Dou, Q. P. Novel dipeptidyl proteasome inhibitors overcome Bcl-2 protective function and selectively accumulate the cyclin-dependent kinase inhibitor p27 and induce apoptosis in transformed, but not normal, human fibroblasts. Cell Death & Diff., in press Dou, Q. P., McGuire, T. F., Peng, Y., An, B. Proteasome inhibition leads to significant reduction of Bcr-Abl expression and subsequent induction of apoptosis in K562 human chronic myelogenous leukemia cells. J Pharm. Exp. Ther. 1999; 289: 781–790.

Fisher D E. Apoptosis in cancer therapy: crossing the threshold. Cell 1994; 78: 539–542.

Harrison, D. J. Molecular mechanisms of drug resistance in tumors. J. Patho. 1995; 175: 7–12.

Milner, J. DNA damage, p53 and cancer therapies. Nature Med. 1995; 1: 789–880.

Bedi, A., Zehnbauer, B. A., Barber, J. P., Sharkis, S. J., Jones, R. J. Inhibition of apoptosis by Bcl-ABL in chronic myeloid leukemia. Blood 1994; 83: 2038–2044.

Mackey, T. J., Borkowski, A., Amin, P., Jacobs, S. C., Kyprianou, N. Bcl-2/bax ratio as a predictive marker for therapeutic response to radiotherapy in patients with prostate cancer. Urology 1998; 52(6): 1085–1089.

Pepper, C., Hoy, T., Bentley, P. Elevated Bcl-2/Bax is a consistent feature of apoptosis resistance in B-cell chronic lymphocytic leukemia and are correlated with vivo chemoresistance. Leuk. Lymphoma 1998; 28(3–4): 355–361.

Molica, S., Dattilo, A., Giulino, C., Levato, D., Levato, L. Increased bcl-2/bax ratio in B-cell chronic lymphocytic leukemia is associated with a progressive pattern of disease. Haematologica 1998; 83(12): 1122–1124.

Krajewski, S., Blomqvist, C., Franssila, K., Krajewska, M., Wasenius, V. M., Niskanen, E., Nordling, S., Reed, J. C. Reduced expression of proapoptotic gene BAX is associated with poor response rates to combination chemotherapy and shorter survival in women with metastatic breast adenocarcinoma. Cancer Res. 1995; 55(19): 4471–4478.

Tai, Y. T., Lee, S., Niloff, E., Weisman, C., Strobel, T., Cannistra, S. A. BAX protein expression and clinical outcome in epithelial ovarian cancer. J. Clin, Oncol 1998; 16(9): 3211.

Harima, Y., Harima, K., Shikata, N., Oka, A., Ohnishi, T., Tanaka, Y. Bax and Bcl-2 expressions predict response to radiotherapy in human cervical cancer. J. Cancer Res. Clin. Oncology 1998; 124(9): 503–510.

McPake, C. R., Tillman, D. M., Poquette, C. A., George, E. O., Houghton, J. A., Harris, L. C. Bax is an important determinant of chemosensitivity in pediatric tumor cell lines independent of bcl-2 expression and p53 status. Oncol. Res. 1998; 10(5): 235–244.

Friess, H., Lu, Z., Graber, H. U., Zimmermann, A., Adler, G., Kore, M., Schmid, R. M., Buchler, M. W. Bax but not bcl-2, influences the prognosis of human pancreatic cancer. Gut 1998; 43(3): 414–421.

White, E. Proc. Soc. Exp. Biol. Med. 1993; 204: 30–39.

Harrington, E. A., Fanidi, A., Evan, G. M. Curr. Opin. Genet. Dev. 1994; 4: 120–129.

Fearnhead, H. O., Rodriguez, J., Govek, E-. E., Guo, W., Kobayashi, R., Hannon, G., Lazebnik, Y. A. Oncogene-dependent apoptosis is mediated by caspase-9. Proc. Natl. Acad. Sci. 1998; 95: 13664–13669.

Li, B. and Dou, Q. P. Proteasome inhibitors overcome Bcl-2 and Bcr-Abl-mediated protection through accumulating bax and subsequently inducing cytochrome c-dependent apoptosis. J. Biol. Chem. 1999; submitted.

Blagosklonny M V, Wu G S, Omura S and el-Deiry W S. Proteasome-dependent regulation of p21 Waf1/Cip1 expression. Biochem. Biophys. Res. Commun. 1996; 227: 564–569

Ciechanover, A. The ubiquitin-proteasome pathway: on protein death and cell life. EMBO J. 1998; 17(24): 7151–7160.

Verma, I. M., Stevenson, J. K., Schwarz, E. M., Antwerp, D. V., Miyamoto, S. Rel/NF-kB/IkB family: intimate tales of association and dissociation. Genes & Development 1995; 9: 2723–2735.

Diehl, J. A., Zindy, F., Sherr, C. J. Inhibition of cyclin D1 phosphorylation on threonine-286 prevents its rapid degradation via the ubiquitin-proteasome pathway. Genes & Development 1997; 11: 957–972.

Won, K.-K., Reed, S. I. Activation of cyclin E/CDK2 is coupled to site-specific autophosphorylation and ubiquitin-dependent degradation of cyclin E. EMBO J. 1996; 15: 4182–4193.

Vlach, J., Hennecke, S. Amati, B. Phosphorylation-dependent degradation of the cyclin-dependent kinase inhibitor p27. EMBO J. 1997; 16: 5334–5344.

Chen, K., Demetris, A. J., Van Thiel, D. H., Whiteside, T. L. Double immunoenzyme staining method for analysis of tissue and blood lymphocyte subsets with monoclonal antibodies. Lab. Invest. 1987; 56: 114–119.

Tomoda, K., Kubota, Y., Kato, J.-Y. Degradation of the cyclin-dependent-kinase inhibitor $p27^{Kip1}$ is instigated by Jab1. Nature 1999; 398: 160–165.

Li, H., Zhu, H., Xu, C-. J., Yuan, J. Cleavage of BID by caspase 8 mediates the mitochondria damage in the Fas pathway of Apoptosis. Cell 1998; 94: 491–501.

Numata, M., Petrecca, K., Lake, N., Orlowski, J. Identification of a mitochondrial $Na^+/H^+$ exchanger. J. Bio. Chem. 1998; 273: 6951–6959.

Martin, S. J., Newmeyer, D. D., Mathias, S., Farschon, D. M., Wang, H., Reed, J. C., Kolesnick, R. N., Green, D. R. Cell-free reconstitution of Fas-, UV-, and ceramide-induced apoptosis. EMBO J. 1995; 14: 1591–5200.

Dignam, J. D., Lebovitz, R. M., Roeder, R. G. Accurate transcription initiation by RNA polymerase II in a soluble extract from isolated mammalian nuclei, Nuclei Acids Res. 1993; 11: 1475–1489.

Bossy-Wetzel, E., Newmeyer, D. D., and Green, D. R. Mitochondrial cytochrome C release in apoptosis occurs upstream of DEVD-specific caspase activation and independent of mitochondrial transmembrane depolarization. EMBO J. 1998; 17: 37–49.

Wood, D. E., Thomas, A., Devi, L. A., Berman, Y., Beavis, R. C., Reed, J. C., and Newcomb, E. W. Bax cleavage is mediated by calpain during drug-induced apoptosis. Oncogene 1998; 17: 1069–1078.

Dou Q P, Levin A H, Zhao S, and Pardee A B. Cyclin E and cyclin A as candidates for the restriction point protein. Cancer Res., 1993; 53: 1493–1497. Goldberg, A. Functions of the proteasome: The lysis at the end of the tunnel. Science 1995; 268: 522–523.

Chau, V., Tobias, J. W., Bachmair, A., Marriot, D., Ecker, D. J., Gonda, D. K., and Varshavsky, A. A multiubiquitin chain is confined to specific lysine in a targeted short-lived protein. Science 1989; 243: 1576–1583.

Palombella, V. J., Rando, O. J. The ubiquitin-proteasome pathway is required for processing the NF-kB1 precursor protein and the activation of NF-kB. Cell 1994; 78: 773–785.

Pagano, M., Tam, S. W., Theodoras, A. M., Beer-Romero, P., Sal, D. G., Chau, V., Yew, P. R., Draetta, G. F., Rolfe, M. Role of the ubiquitin-proteasome pathway in regulating abundance of the cyclin-dependent kinase inhibitor p27. Science 1995; 269: 682–685.

Li, B., Kanamaru, H., Noriki, S., Yamaguchi, T., Fukuda, M., Okada, K. Reciprocal expression of bcl-2 and p53 oncoproteins in urothelial dysplasia and carcinoma of the urinary bladder. Urol. Res. 1998; 26: 235–241.

Bargou, R. C., Wagener, C., Bommert, K., Mapara, M. Y., Daniel, P. T., Arnold, W., Dietel, M., Guski, H., Feller, A., Royer, H. D., Dorken, B. Overexpression of the death-promoting gene bax-alpha which is downregulated in breast cancer restores sensitivity to different apoptotic stimuli and reduces tumor growth in SCID mice. J. Clin. Invest. 1996; 97: 2651–2659.

Binder, C., Marx, D., Binder, L., Schauer, A., Hiddemann, W. Expression of Bax in relation to Bcl-2 and other predictive parameters in breast cancer. Ann, Oncol. 1996; 7(2): 129–133.

Su. Z. Z., Madireddi, M. T., Lin, J. J., Young, C. S., Kitada, S., Reed, J. C., Goldstein, N. I., Fisher, P. B. The cancer growth suppressor gene mda-7 selectively induces apoptosis in human breast cancer cells and inhibits tumor growth in nude mice. Proc. Natl. Acad. Sci. 1998; 95(24): 14400–14405.

Xiao, G., Liu, Y. E., Gentz, R., Sang, Q. A., Ni, J., Goldberg, I. D., Shi, Y. E. Suppression of breast cancer growth and metastasis by a serpin myoepithelium-derived serine proteinase inhibitor expressed in the mammary myoepithelial cells. Proc. Natl. Acad. Sci. 1999; 96(7): 3700–3705.

Koshizuka, K., Kubota, T., Said, J., Koike, M., Binderup, L., Uskokovic, M., Koeffler, H. P. Combination therapy of a vitamin D3 analog and all-trans-retionic acid: effect on human breast cancer in nude mice. Anticancer Res. 1999; 19(1A): 519–524.

Orlowski, R. Z., Eswars, J. R., Lafond-Walker, A., Grever, M. R., Orlowski, M., Dang, C. V. Tumor growth inhibition induced in a murine model of human Burkitt's lymphoma by a proteasome inhibitor. Cancer Res. 1998; 58(19): 4342–4348.

Corbett, T., Valeriote, F., LoRusso, P., Polin, L., Panchapor, C., Pugh, S., White, K., Knight, J., Demchjik, L., Jones, J., Jones, L., and Lisow, L. In vivo methods for screening and preclinical testing: use of rodent solid tumors for drug discovery. In: B. A. Teicher (ed.) Anticancer Drug Development Guide: Preclinical Screening, Clinical Trials, and Approval, Totowa, N.J.: Humana Press, Inc., 1997.

Portera-Cailliau, C., Sung, C.-H., Nathans, J., and Adler, R. Apoptotic photoreceptor cell death in mouse models of retinitis pimentosa. Proc. Natl. Acad. Sci. 1994; 91: 974–978.

Sun, J., Qian, Y., Hamilton A. D., and Sebti, S. M. Both farnesyltransferase and geranylgeranyltransferase I inhibitors are required for inhibition of oncogenic K-Ras prenylation but each alone is sufficient to suppress human tumor growth in nude mouse xenografts. Oncogene 1998; 16: 1467–1473.

Miura, M., Zhu, H., Rotollo, R., Hartweig, E. A, Yuan, J. Induction of apoptosis in fibroblasts by IL-1b-converting enzyme, a mammalian homologue of the *C. elegant* cell death gene ced-3. Cell 1993; 75: 653–660.

Ezhevsky, S. A., Nagagara, H., Vocero-Akbani, A. M., Gius, D. R., Wei, M. C., and Dowdy. S. F. Hypophosphorylation of the retinoblastoma protein (pRb) by cyclin D:CDK4/6 complexes results in active pRb. Proc. Natl. Acad. Sci. 1997; 94: 10699–10704.

Chen, G., Ray, R., Dubik, D., Shi, L., Cizeau, J., Bleackley, C. R., Saxena, S., Gietz, R. D., Greenberg, A. H. The E1B 19K/Bcl-2-binding protein Nip3 is a dimeric mitochondrial protein that activates apoptosis. J. Exp. Med. 1997; 186: 1975–1983.

Chen, G., Cizeau, J., Vande, V. C., Park, J. H., Bozek, G., Bolton, J., Shi, L., Dubik, D., Greenberg, A. H. Nix and Nip3 form a subfamily of pro-apoptotic mitochondrial proteins. J. Biol. Chem. 1999; 274(1): 7–10.

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial sequence
<220> FEATURE:
<221> NAME/KEY: Artificial sequence
<222> LOCATION: (1)..(25)
<223> OTHER INFORMATION: primer

<400> SEQUENCE: 1
cagctctgag cagatcatga agaca                                          25

<210> SEQ ID NO 2
<211> LENGTH: 25
<212> TYPE: DNA
<213> ORGANISM: Artificial sequence
<220> FEATURE:
<221> NAME/KEY: Artificial sequence
<222> LOCATION: (1)..(25)
<223> OTHER INFORMATION: primer

<400> SEQUENCE: 2
gcccatcttc ttccagatgg tgagc                                          25
```

Plowman, J. Dykes, D. J., Hollingshead, M., Simpson-Herren, L., and Alley, M. C. Human tumor xenograft models in NCI drug development. In: B. A. Teicher (ed.), Anticancer Drug Development guide: Preclinical Screening, Clinical Trials, and Approval. Totowa, N.J.: Humana Press. Inc 1997.

What is claimed is:

1. A method for assaying a sample for Bax protein degradation activity, said method comprising:

a) incubating a labeled Bax protein with a protein extract prepared from said sample; and b) detecting the level of label present in the sample, wherein a decreased signal is indicative of increased Bax degradation activity.

2. The method according to claim 1, wherein the incubated Bax protein is subjected to size fractionation following step (a).

3. The method according to claim 2, wherein said size fractionation comprises gel electrophoresis.

4. The method according to claim 1, wherein said sample is from an animal.

5. The method according to claim 4, wherein said sample is a sample of bodily fluids or tissues.

6. The method according to claim 4, wherein said animal is a human.

7. The method according to claim 1, wherein said Bax protein is incubated with said protein extract in step (a) for 2 to 4 hours.

8. The method according to claim 1, wherein said Bax protein is incubated with said protein extract in step (a) at 37° C.

9. The method according to claim 1, wherein said protein extract comprises proteasome.

10. The method according to claim 1, wherein said Bax protein is labeled with a label that provides a detectable signal.

11. The method according to claim 10, wherein said label is selected from the group consisting of a chemiluminescent label, a fluorescent label, a radiolabel, and an enzymatic label.

12. The method according to claim 10, wherein said label is a radiolabel.

13. The method according to claim 12, wherein said radiolabel is detected by autoradiography.

14. The method according to claim 13, wherein said radiolabel is $^{35}$S or $^{32}$P.

15. The method according to claim 1, wherein said level of degradation of said Bax protein is determined by the binding of an anti-Bax antibody to Bax protein following step (a).

16. The method according to claim 1, wherein said sample comprises tumor cells or cancer cells.

17. The method according to claim 9, wherein said proteasome is purified 20S proteasome.

* * * * *

UNITED STATES PATENT AND TRADEMARK OFFICE
CERTIFICATE OF CORRECTION

PATENT NO. : 6,692,927 B2
DATED : February 17, 2004
INVENTOR(S) : Ping Dou and Benyi Li It is certified that error appears in the above-identified patent and that said Letters Patent is hereby corrected as shown below:

Column 1,
Lines 51 and 67, "BcL-XL" should read -- BcL-$X_L$ --.

Column 3,
Line 49, "patents" should read -- patients --.

Signed and Sealed this

Twenty-ninth Day of June, 2004

JON W. DUDAS
*Acting Director of the United States Patent and Trademark Office*